US009132027B2

(12) United States Patent
Calco

(10) Patent No.: US 9,132,027 B2
(45) Date of Patent: Sep. 15, 2015

(54) ADJUSTABLE CERVICAL COLLAR

(71) Applicant: Wayne A Calco, Aliso Viejo, CA (US)

(72) Inventor: Wayne A Calco, Aliso Viejo, CA (US)

( * ) Notice: Subject to any disclaimer, the term of this patent is extended or adjusted under 35 U.S.C. 154(b) by 188 days.

(21) Appl. No.: 13/831,852

(22) Filed: Mar. 15, 2013

(65) Prior Publication Data

US 2014/0012172 A1  Jan. 9, 2014

Related U.S. Application Data

(60) Provisional application No. 61/668,727, filed on Jul. 6, 2012.

(51) Int. Cl.
*A61F 5/00* (2006.01)
*A61F 5/055* (2006.01)

(52) U.S. Cl.
CPC ...................................... *A61F 5/055* (2013.01)

(58) Field of Classification Search
CPC ................... A63B 2210/50; A63B 2021/0612;
A63B 21/068; A63B 22/0023; A63B 22/0087;
A63B 21/015; A63B 21/0611; A63B 21/154;
A63B 2208/0252; A63B 2210/58; A63B
22/0605; A63B 23/12; A63B 2022/0652;
A61M 16/0057; A61M 16/06; A61M 16/0616;
A61M 16/0683; B61D 33/005
USPC ................................ 602/17–19; 128/DIG. 23
See application file for complete search history.

(56) References Cited

U.S. PATENT DOCUMENTS

| 2,088,207 | A | * | 7/1937 | Kaiser ............................ 297/392 |
| 2,791,999 | A | | 9/1954 | Bustamante |
| 4,643,174 | A | * | 2/1987 | Horiuchi .......................... 602/18 |
| 4,886,052 | A | * | 12/1989 | Calabrese ........................ 602/18 |
| 5,180,361 | A | | 1/1993 | Moore et al. |
| 5,230,698 | A | | 7/1993 | Garth |
| 5,588,957 | A | | 12/1996 | Martin, Sr. |
| 6,090,058 | A | | 7/2000 | Traut et al. |
| 7,128,724 | B2 | | 10/2006 | Marsh |
| 7,141,031 | B2 | | 11/2006 | Garth et al. |

(Continued)

FOREIGN PATENT DOCUMENTS

CN        202 015 274 U    10/2011

OTHER PUBLICATIONS

Invitation to Pay Additional Fees, Communication of Partial Search Report, International Application PCT/US2013/049475, mailed Nov. 15, 2013.

(Continued)

*Primary Examiner* — Michael Brown
(74) *Attorney, Agent, or Firm* — Larry K. Roberts

(57) ABSTRACT

An embodiment of an adjustable cervical collar system includes a collar body and a chin support structure assembled together, about respective pivots at opposed ends, for pivotal movement about a pivot axis so that the angle subtended by the collar body and chin support structure can be adjusted. The collar body and chin support structure can be locked in a selected position by a locking mechanism. A release mechanism permits the wearer to release the locking mechanism using one hand, and the angular position of the chin support structure relative to the collar body is changed manually. When the release mechanism is released, the locking mechanism automatically locks the chin support in the new position. A neck strap is detachable from the chin support structure and the collar body, and its length is also adjustable.

21 Claims, 22 Drawing Sheets

(56) References Cited

U.S. PATENT DOCUMENTS

| | | |
|---|---|---|
| 7,371,222 B2 | 5/2008 | Heinz et al. |
| 7,399,288 B2 | 7/2008 | Chao |
| 7,674,234 B2 | 3/2010 | Calco et al. |
| 7,846,117 B2 | 12/2010 | Leatt et al. |
| 8,038,635 B2 | 10/2011 | Dellanno |
| 8,038,636 B2 | 10/2011 | Thorgilsdottir et al. |
| 8,216,167 B2 | 7/2012 | Garth et al. |
| 2007/0027418 A1 | 2/2007 | Calco et al. |
| 2012/0053499 A1 | 3/2012 | Donaldson et al. |
| 2012/0130295 A1 | 5/2012 | Haider |
| 2013/0060179 A1 | 3/2013 | Modglin |

OTHER PUBLICATIONS

Notification of Transmittal of International Search Report and Written Opinion of International Searching Authority, International Application PCT/US2013/049475, mailed Jan. 21, 2014.

* cited by examiner

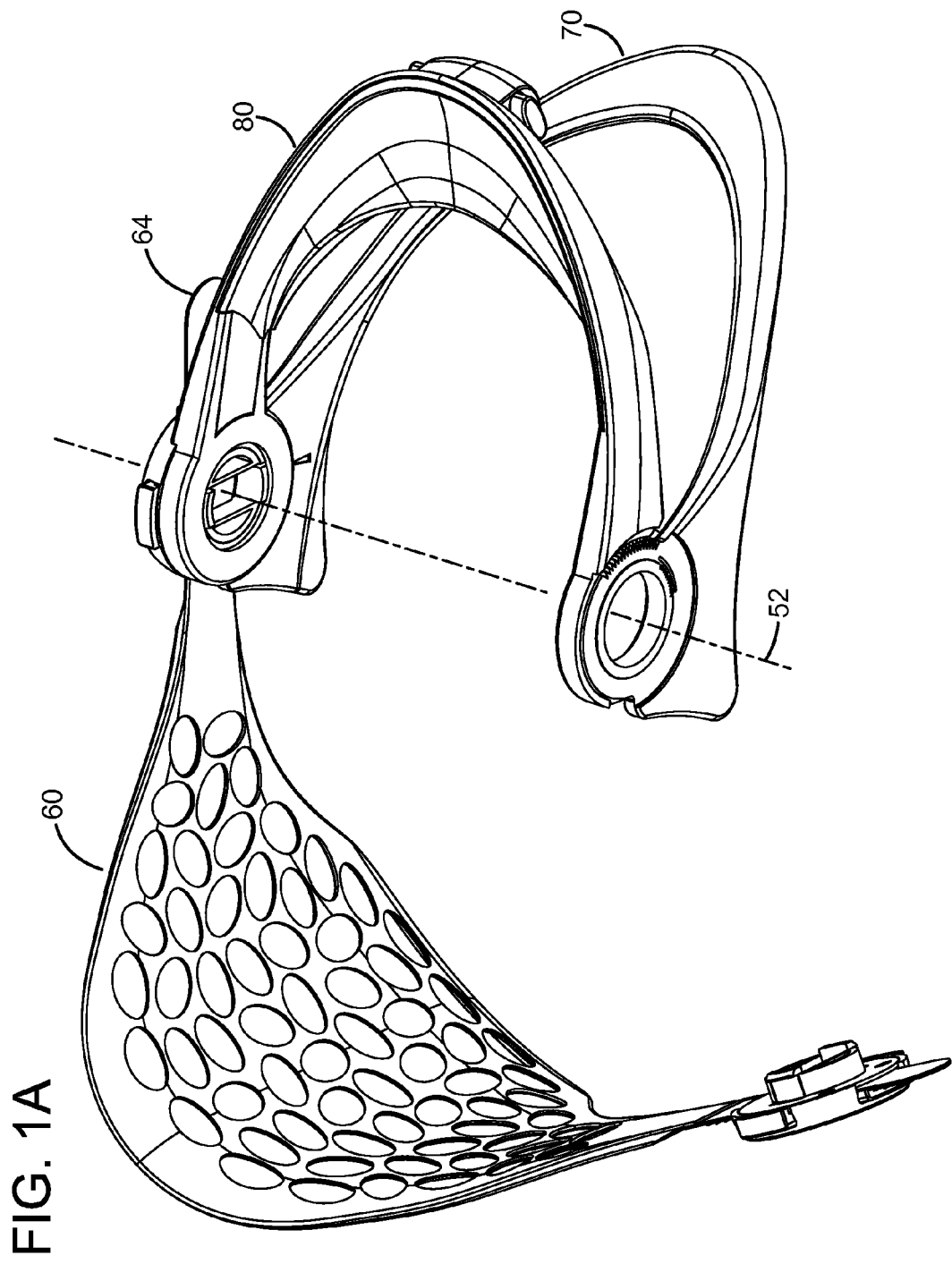

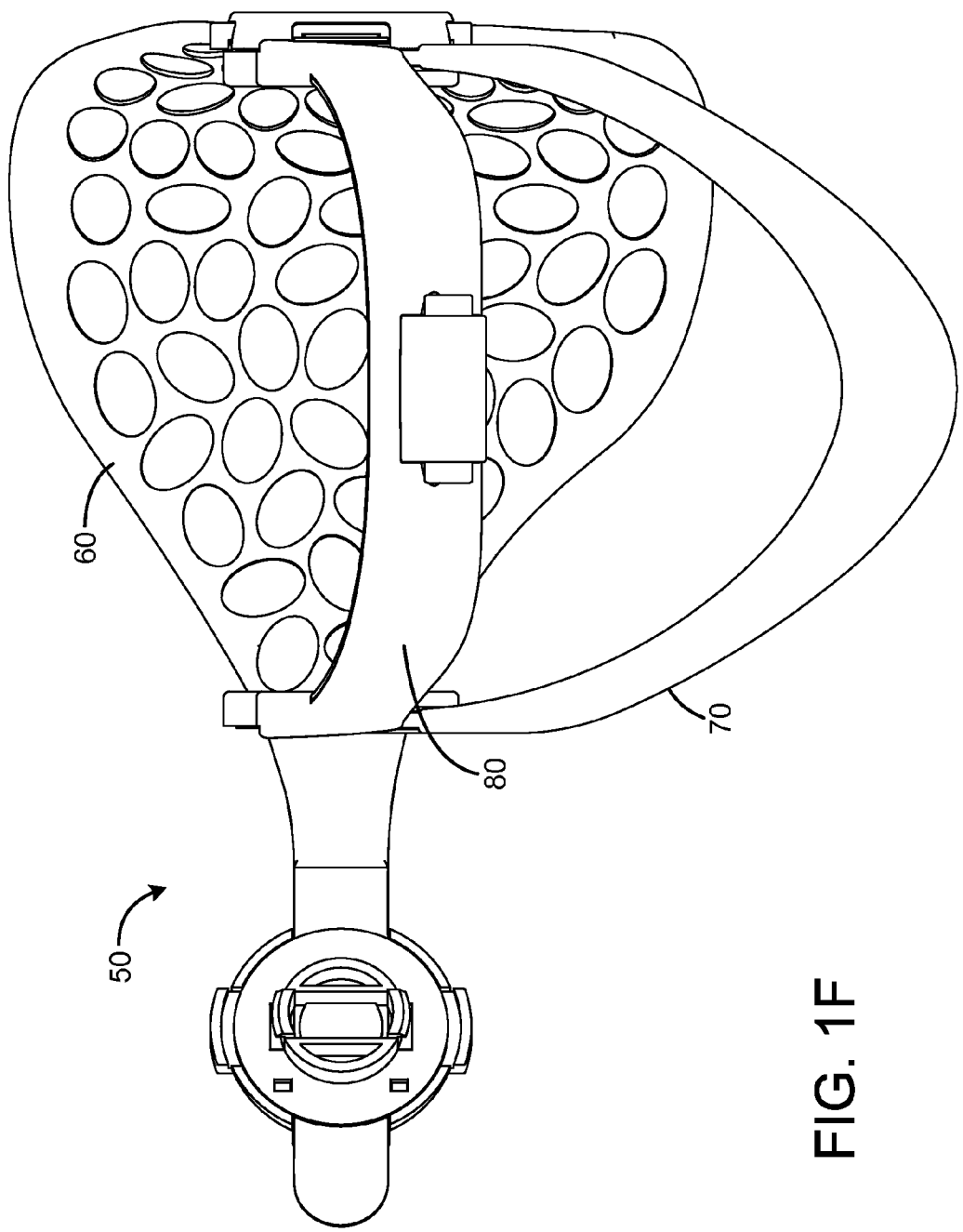

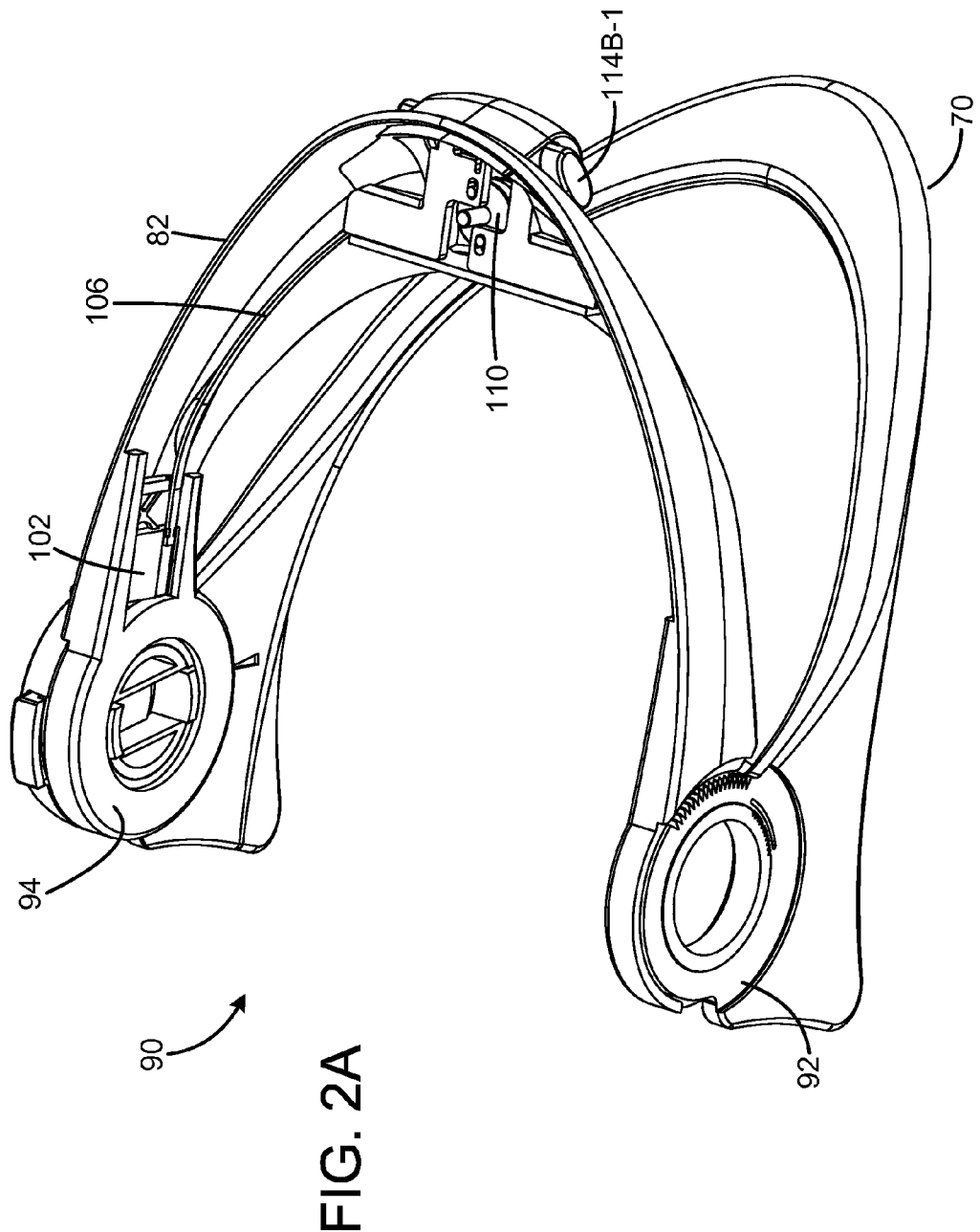

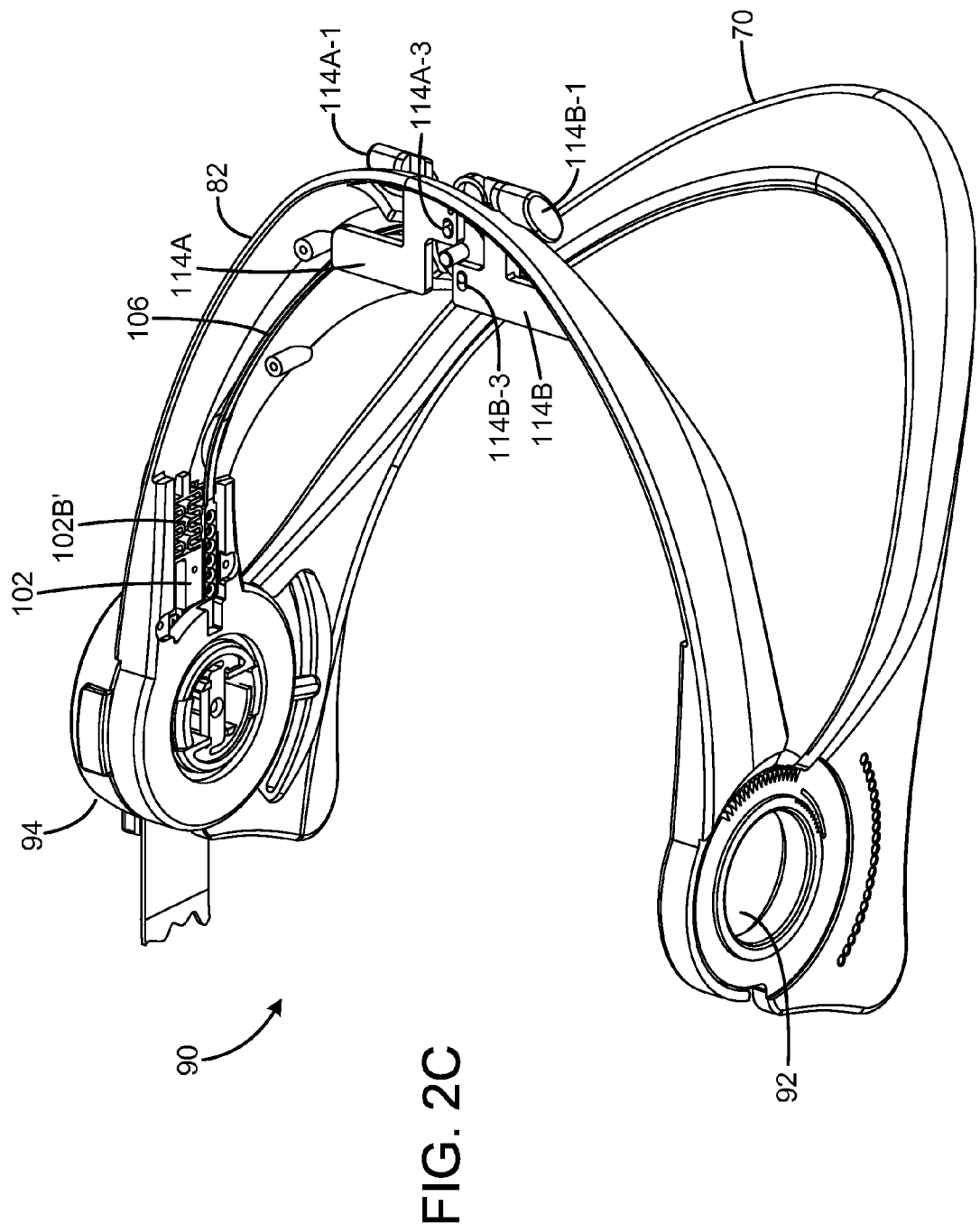

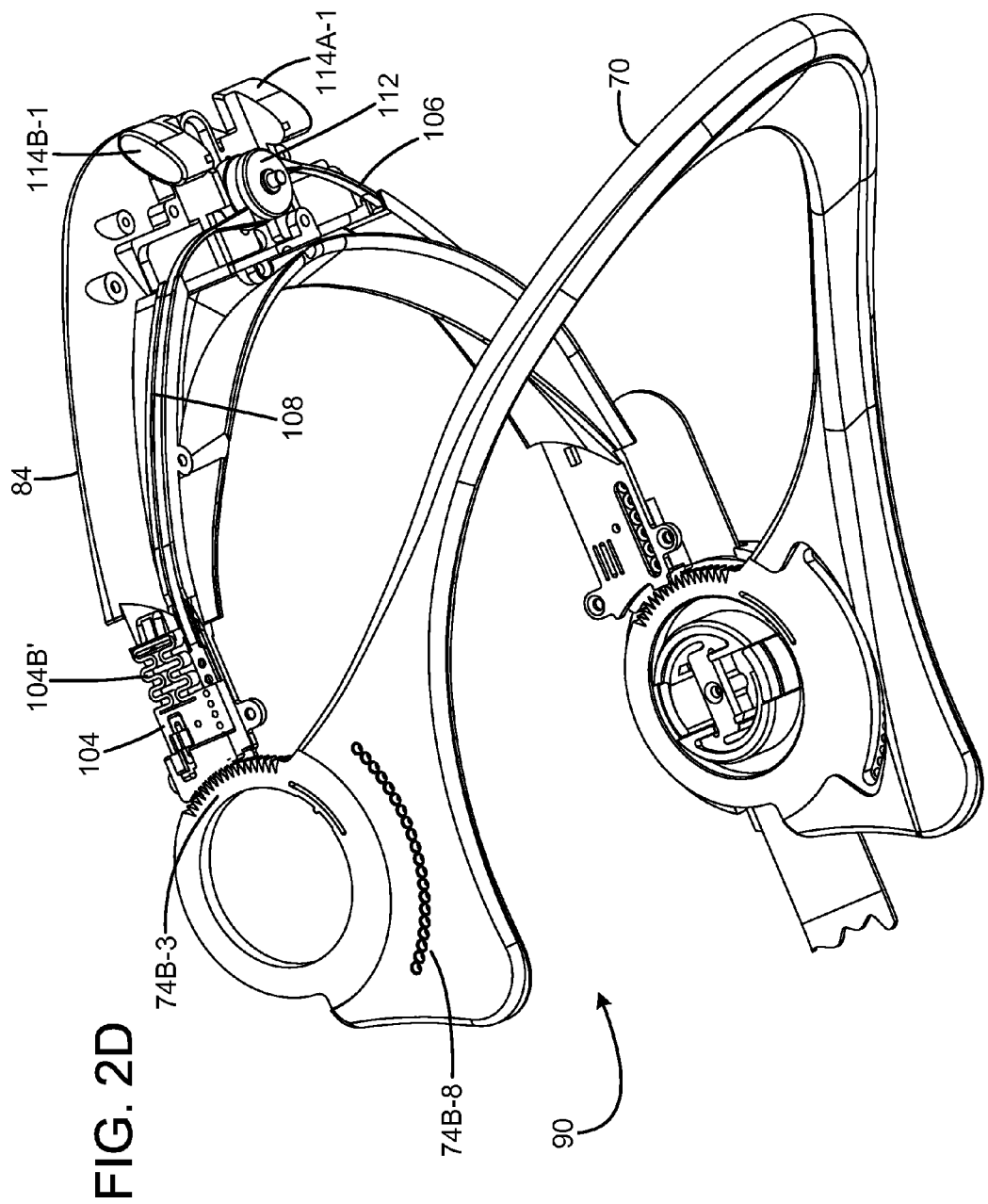

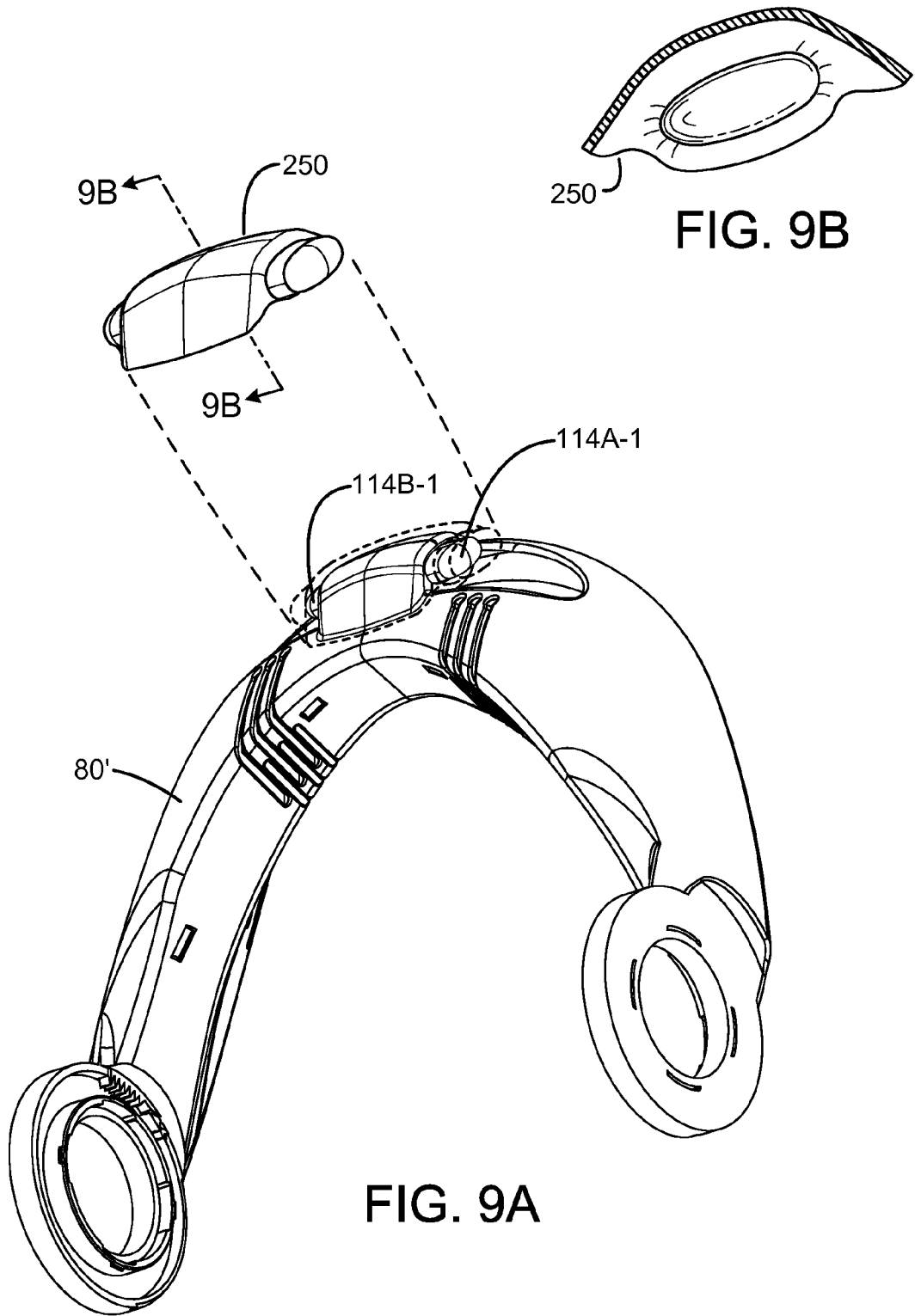

ADJUSTABLE CERVICAL COLLAR

CROSS-REFERENCE TO RELATED PATENT APPLICATIONS

This application claims priority to and the benefit of U.S. Provisional Patent Application No. 61/668,727, filed Jul. 6, 2012.

BACKGROUND

Cervical collars are used to support a person's neck and head for various therapeutic, comfort and emergency uses. Some collars are adjustable, and ease of adjustment and fitting to a particular person is desirable.

BRIEF DESCRIPTION OF THE DRAWINGS

Features and advantages of the disclosure will readily be appreciated by persons skilled in the art from the following detailed description when read in conjunction with the drawing wherein:

FIGS. 1A and 1B are respective isometric views of an exemplary embodiment of an adjustable cervical collar with one side of a neck strap detached from its right side connection, taken from an upper left and lower right orientation. FIG. 1F is a front view of the collar as in FIG. 1E.

FIG. 2A and 2B are isometric views of the cervical collar as in respective FIGS. 1A and 1B, with the neck strap removed, and the chin support housing partially removed. FIGS. 2C and 2D are views similar to FIGS. 2A and 2B, but showing an alternate embodiment of a spring feature.

FIGS. 9A-9B illustrate another embodiment of a lock for preventing operation of a release mechanism for an adjustable collar body system.

DETAILED DESCRIPTION

Figure 1B:
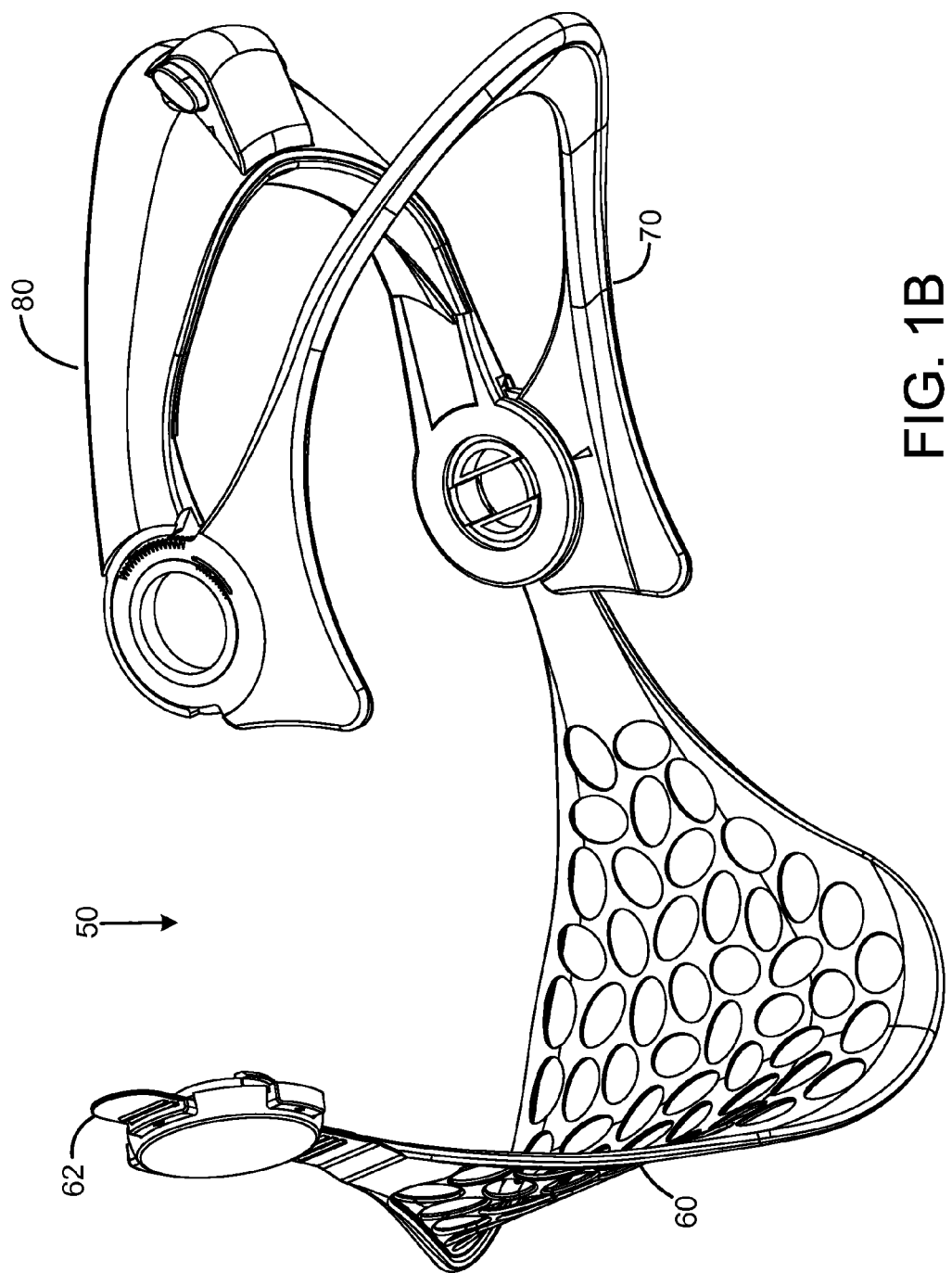
Figure 1C:
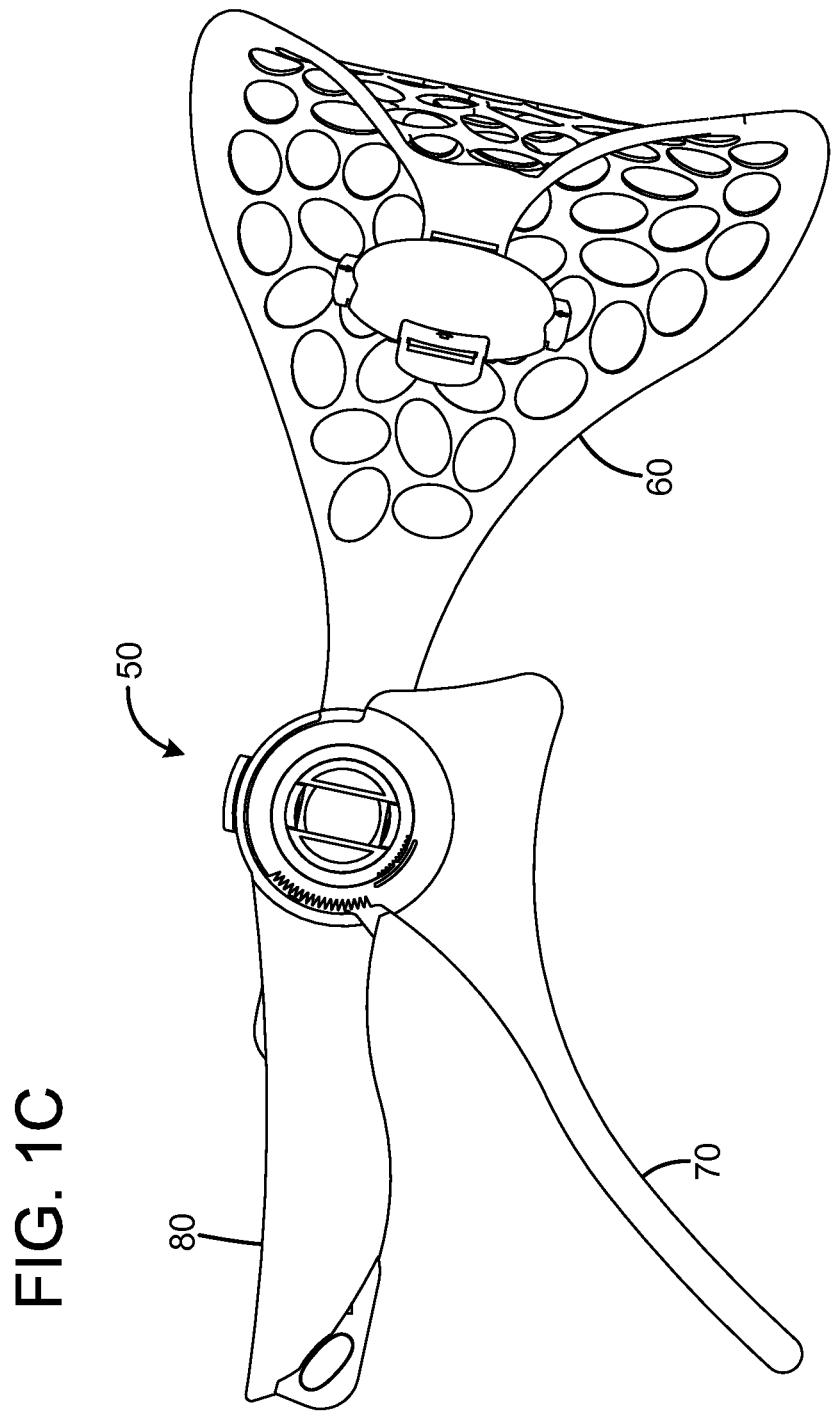
FIG. 1C is a left side view of the collar, showing the neck strap detached from its left side connection.
Figure 1D:
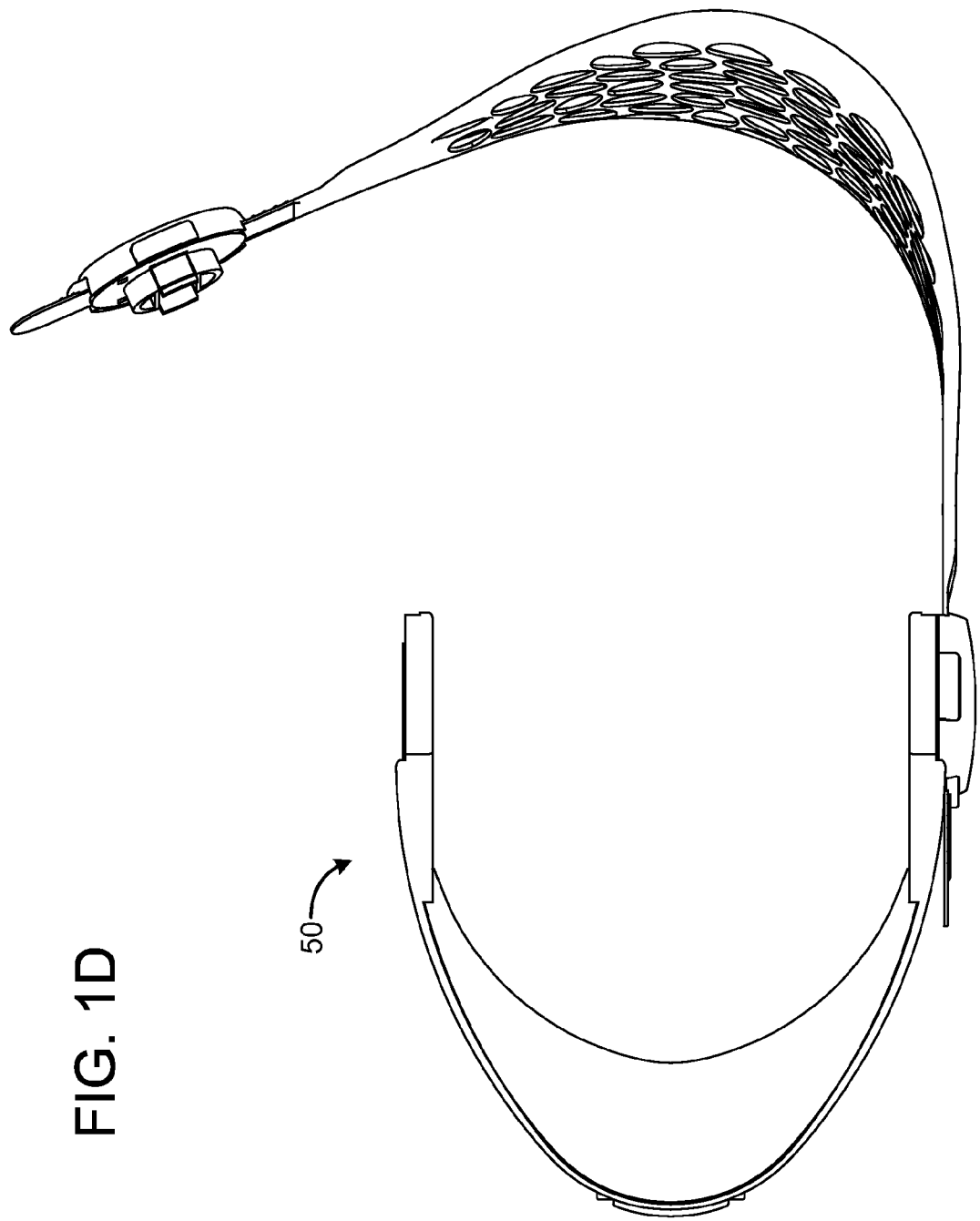
FIG. 1D is a bottom view of the collar as in FIG. 1C.
Figure 1E:
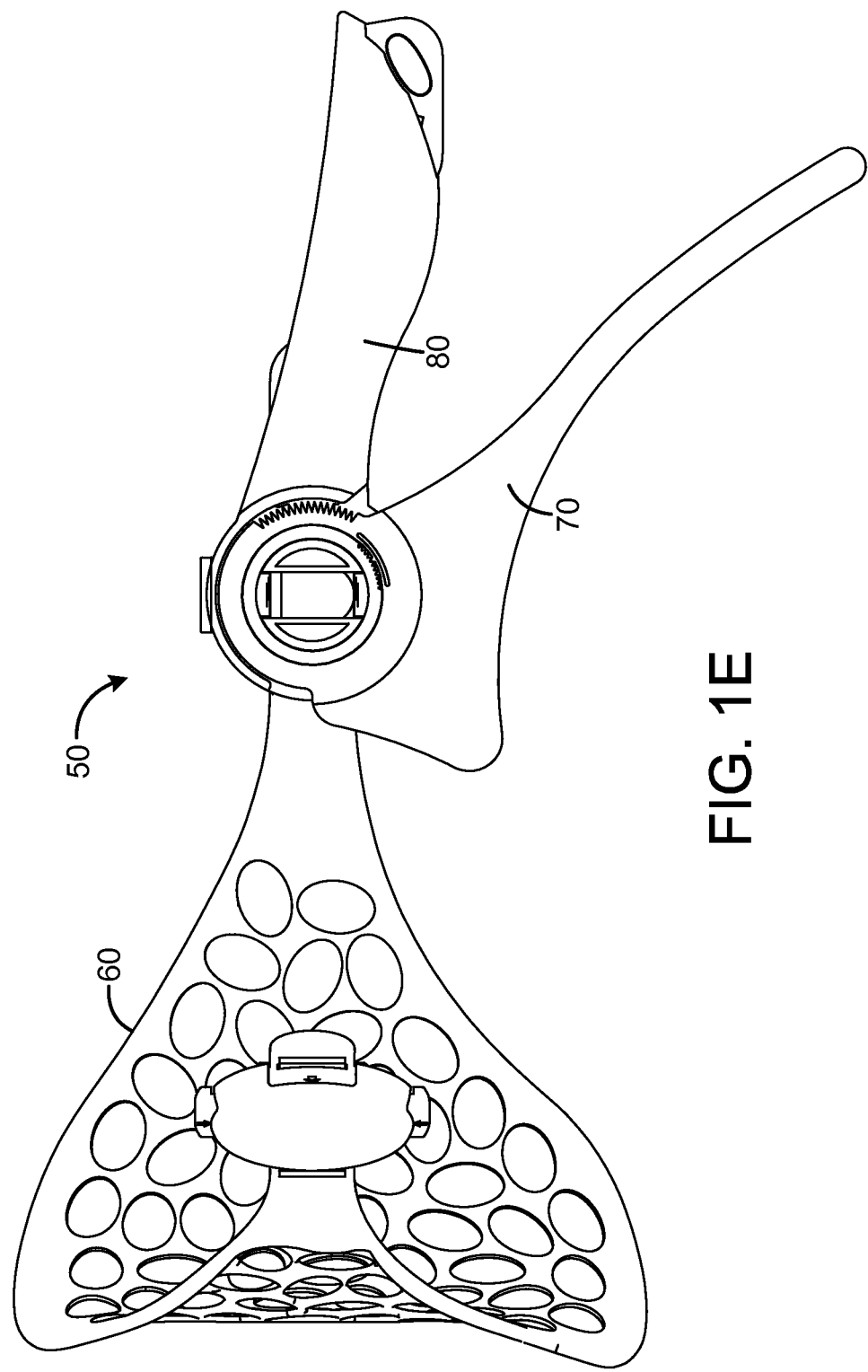
FIG. 1E is a right side view of the collar as in FIG. 1A.

In the following detailed description and in the several figures of the drawing, like elements are identified with like reference numerals. The figures may not be to scale, and relative feature sizes may be exaggerated for illustrative purposes.

An exemplary embodiment of an adjustable cervical collar system 50 is illustrated in FIGS. 1A-5B. The collar system includes a neck strap 60, a collar body 70, and a chin support structure 80. The collar body and chin support structure are assembled together, about respective pivots at each end, and arranged for pivotal movement about a pivot axis 52 so that the angle subtended by the collar body and chin support structure can be adjusted through an angular range, and the structures 70 and 80 locked in a selected position by a locking mechanism. The system includes a release mechanism permitting the wearer to easily release the locking mechanism, using one hand, and the angular position of the chin support structure relative to the collar body is changed manually. When the release mechanism is released, the locking mechanism automatically locks the chin support in the new position. The neck strap 60 is detachable from the chin support structure and the collar body, and its length is also adjustable.

Figure 3:
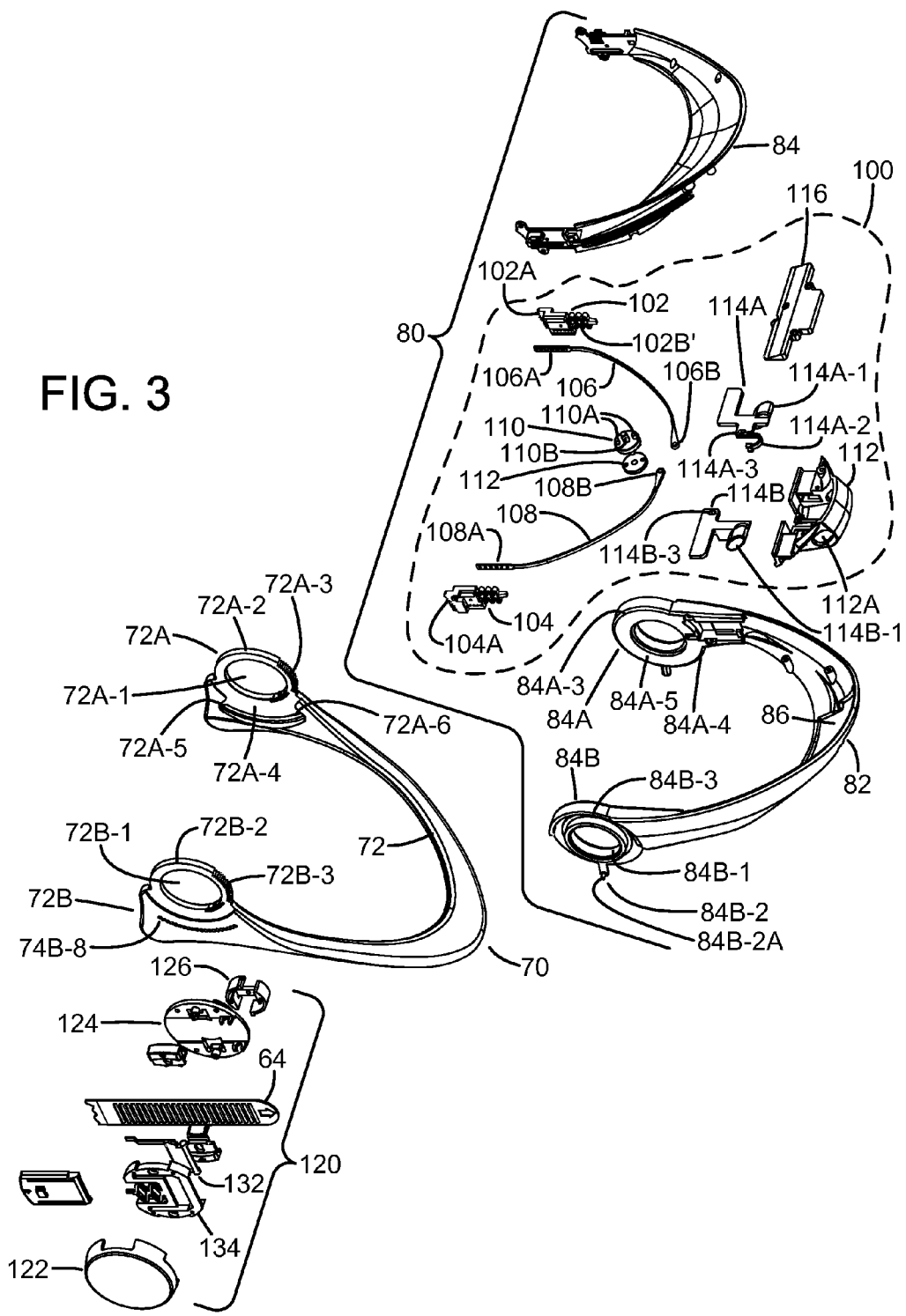
FIG. 3 is an exploded isometric view of the cervical collar arrangement as illustrated in FIGS. 2C and 2D, and the connection between the neck strap and the pivot connection.

FIG. 3 is an exploded view of features of an exemplary embodiment of the collar system, including the collar body 70 and the chin support structure 80.

In an exemplary embodiment, the collar body 70 is a unitary rigid one-piece structure, preferably fabricated by injection molding a plastic material, such as polypropylene, polyamide, polycarbonate or other suitable material which becomes rigid when cured or cooled. The collar body includes an arcuate portion 72, having end portions 72A and 72B. The end portions have peripheral portions 72A-2 and 72B-2 defining circular openings 72A-1 and 72B-1, respectively. The peripheral portions each have a series of locking teeth 72A-3 and 72B-3 formed on the exterior surfaces, and the teeth form part of the locking mechanism described above.

The chin support structure 80 includes a rigid lower housing structure 82 and a rigid upper housing structure 84, which are assembled together by threaded fasteners, or in other suitable ways, such as snap fit or adhesive. The housing structures 82 and 84 are respective unitary one-piece structures, which in an exemplary embodiment are fabricated by injection molding a plastic material, such as polypropylene, polyamide, polycarbonate or other suitable material which becomes rigid when cured or cooled. The exploded view of FIG. 3 shows the elements of an exemplary locking and release mechanism 100, which are fitted within the assembled housing structures.

Figure 2B:
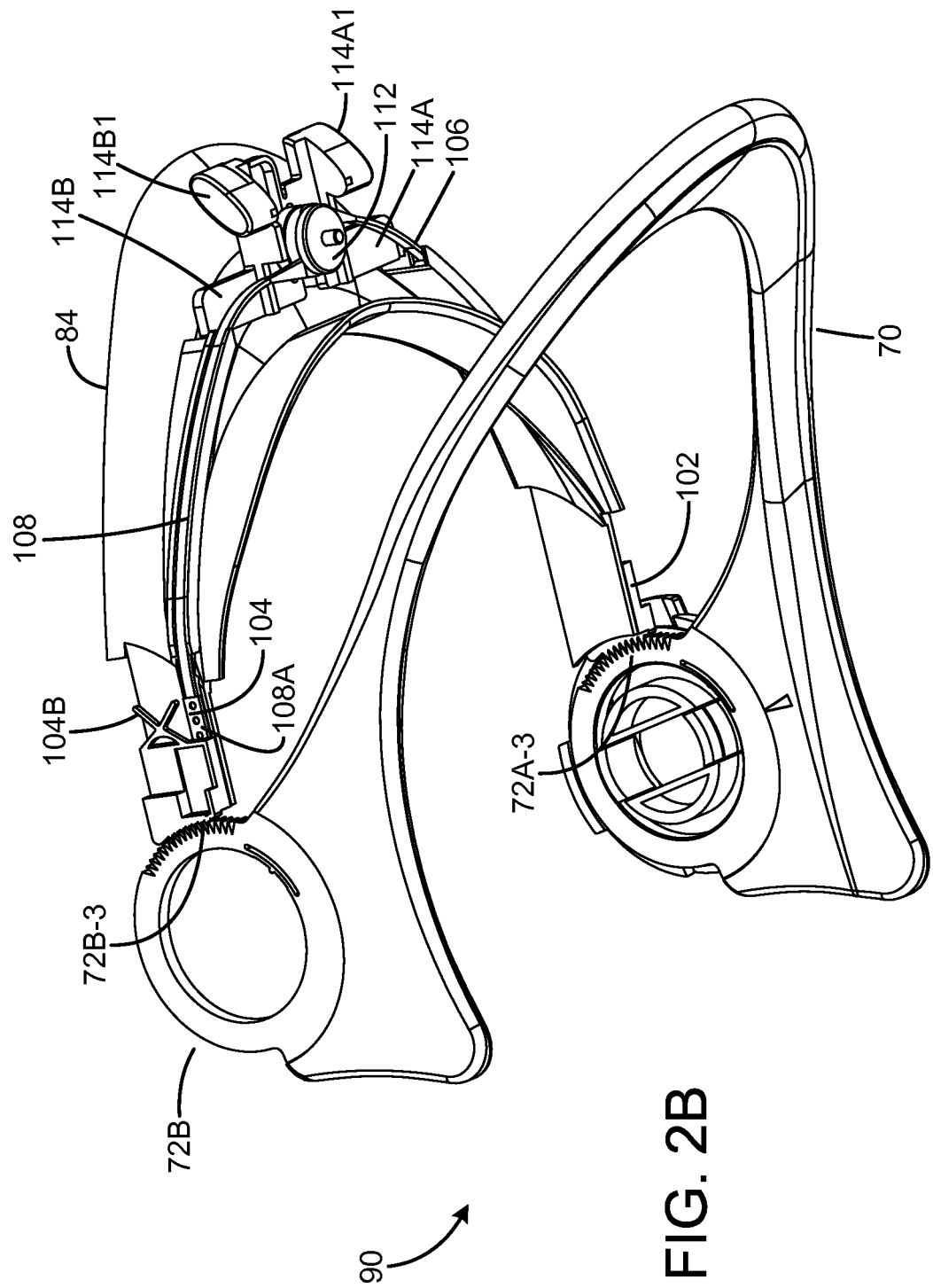

FIGS. 2A-2B show the assembly 90 of the collar body 70 and chin support structure 80 in different states. In FIG. 2A, the upper housing structure 84 is not shown. In FIG. 2B, the lower housing structure 82 is not shown, and the upper housing structure is partially broken-away to reveal sliding member 104 and X-shaped spring 104B, with cable end 108A of cable 108 attached to the sliding member 104. The X-shaped spring applies a bias force tending to push the sliding member 104 and its teeth 104A into engagement with the collar body teeth 72B-3. A pulling force applied to the sliding member 104 can compress the spring 104B, to move the teeth 104A out of engagement with the collar body teeth 72B-3. Sliding member 102 operates in a similar manner.

FIGS. 2C-2D are similar to FIGS. 2A-2B, but illustrate an alternate embodiment of a spring to apply bias force on the sliding members 102, 104. The alternate embodiment includes 104B' which may be integrally formed as part of sliding member 104, from a plastic material, The spring 104B' is formed with serpentine elements, which may be compressed by a pulling force tending to pull the sliding member 104 away from the collar body teeth 72B-3.

The lower housing structure 82 includes respective connector end portions 84A, 84B, which are cooperatively configured with the end portions 72A, 72B of the collar body 70 such that the connector end portions 82A, 82B are fitted into the circular openings 72A-1 and 72B-1 and allow pivotal movement of the chin support structure about the pivot axis 52. In this exemplary embodiment, the connector end portions define circular bosses such as 84B-1 protruding within an outer shroud portion 84B-3. The circular boss, e.g. 84B-1, fits within the peripheral portion, e.g. 72B-2, of the end portion 72B, and acts as a bearing surface. A tab 84B-2 protrudes from the circular boss, and a pin, such as pin 84B-2A, protrudes from the tip of the tab in a transverse direction, and rides over a series of small openings 74B-8 formed in the peripheral portion of the collar body, so as to provide a visual indication of the angular position of the chin support structure relative to the collar body. The housing structure 82 is a rigid structure, and the distance between the connector end portions 84A, 84B is slightly longer than the distance between the end portions 72A, 72B of the collar body. the ends of the collar body may be spread partly apart, or the ends of the chin support pressed together slightly to allow the assembly of the connector end portions into the end portions of the collar body, and the natural tension of the juxtaposition of the chin support with the collar body will maintain the assembled condition.

The collar system 50 includes a releasable locking system 100 to lock the chin support structure 80 in a desired rotational position relative to the collar body 70. The locking system includes the lines of teeth 72A-3 and 72A-4 formed on the outer surfaces of the peripheral portions 72A-2 and 72B-2, which are engaged by teeth formed at the end of sliding members 102, 104 carried within the chin support housings 82 and 84 and constrained for some movement along an axis toward and away from the teeth on the collar body. The sliding members are biased toward the collar body teeth by spring members, so that the default or rest positions of the sliding members are in the locked or engagement positions with the collar body teeth. First ends 106A, 108A of flexible cables 106, 108 are attached to the respective sliding members 102, 104 to provide a means to pull the teeth of the sliding members against the spring bias force and out of engagement with the collar body teeth, to release the lock. The user may then rotate the chin support structure to a desired position relative to the collar body, with the locking system in the unlocked or released condition. Releasing tension on the cables 106, 108 allows the spring force (applied by springs such as 104B or 104B') to automatically pull the sliding members back to the locked condition at the desired position.

The releasable locking system 100 further includes a mechanism operable by the user to exert pulling force on the cable ends 106B, 108B. In an exemplary embodiment, this mechanism includes a wheel assembly of wheels 110, 112 mounted for rotation about center shaft 110B, with pins 110A protruding from the wheel assembly at opposed locations adjacent the wheel periphery. The cable ends 106B, 108B have eyelets which are connected onto respective ones of the pins 110A, and sandwiched between wheels 110, 112. By rotating the wheel assembly, opposed pulling forces are exerted on the cable ends and thereby on the sliding members 102, 104, pulling the teeth on the sliding members out of engagement with the collar body teeth and releasing the lock.

In an exemplary embodiment, the mechanism to exert pulling force on the cable ends further includes housing 112, back plate 116 and actuating arms 114A, 114B. The actuating arms are mounted in the housing 112, each having a button portion 114A-1 and 114B-1 which protrude through openings 112A on opposite sides of the front of the housing 112. A spring 114A-2 on an arm 114A provides a separating force tending to push the respective button portions away from each other. The actuating arms 114A, 114B have respective slot openings 114A-3, 114B-3 which are engaged by respective pins 110A of the wheel 110. The respective slot openings 114A-3, 114B-3 are offset to allow engagement with the pins disposed at opposed locations on the wheel periphery. The user can grip the buttons between two fingers and press the two buttons toward each other, and thus actuating the wheel assembly to exert pulling forces on the cables. When the user releases the buttons, the pulling force is released, and the locking mechanism is in a locked position. Other suitable mechanisms may also be employed to rotate the wheel assembly 110, 112.

The lower housing 82 includes channel features in which the sliding members are mounted. An opening such as 84A-4 in each shroud portion (such as 82A-3) of the housing 82 allows the toothed end of the sliding member to pass into engagement with the collar body teeth.

The spring members (such as 1048, 104B' may be fabricated of a material such as nylon. An exemplary suitable material for the cables 106, 108 is Delrin™ but other material may alternatively be employed. The cables may be attached to the sliding members by snap fit, adhesive, fasteners, or even by integral molding of the parts.

The neck strap 60 is attached at each end to the pivot connections of the collar body and chin support structure by a strap connector. An exemplary connector 120 is illustrated in FIGS. 3 and 4A-4C. The connector 120 includes a housing member 122 and a back plate 124 assembled to the housing member by threaded fasteners. The strap 60 in an exemplary embodiment is a unitary flexible or semi-rigid material, such as nylon or polyethylene.

The strap connector 120 provides the functions of adjusting the effective strap length and allowing easy connection and disconnection of the strap connector from the collar body and chin support structure. The connector 120 also allows for rotation of the connector about the connection to the collar body. Respective clip members 128A, 128B are mounted in the housing 122 and retained by the back plate, and each includes a button portion (128A-2, 128B-2) and a clip barb feature (128A-1, 128B-1). A spring member 126 is mounted in a protruding boss feature 124A of the back plate, and provides a bias force tending to push the barb features apart. The barb features 128A-1, 128B-1 are configured to pass through the opening in the connector ends of the collar body 70, and to clip over the interior surface such as 84A-5 of the lower housing structure 82, thus securing the connector 120 in place. The button portions 128A-2, 128B-2 protrude through slots 122B in the housing structure 122, and the user, by pressing the respective button portions together, urge the respective barb portions toward each other and out of engagement with the collar body and chin support structure, allowing the connector to be removed. Another feature is that the connectors 120 allow the neck strap to be removed from the collar body and chin support structure, without changing or affecting the effective strap length.

Figure 4B:
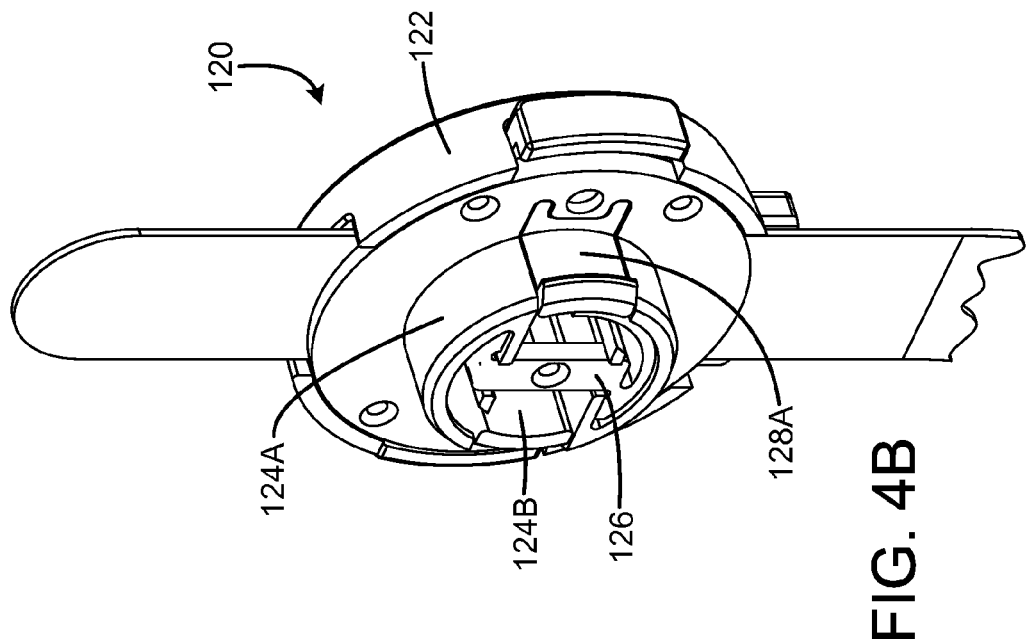
FIGS. 4A and 4B are respective front and back isometric views of one exemplary strap connection to the collar pivot.
Figure 4A:
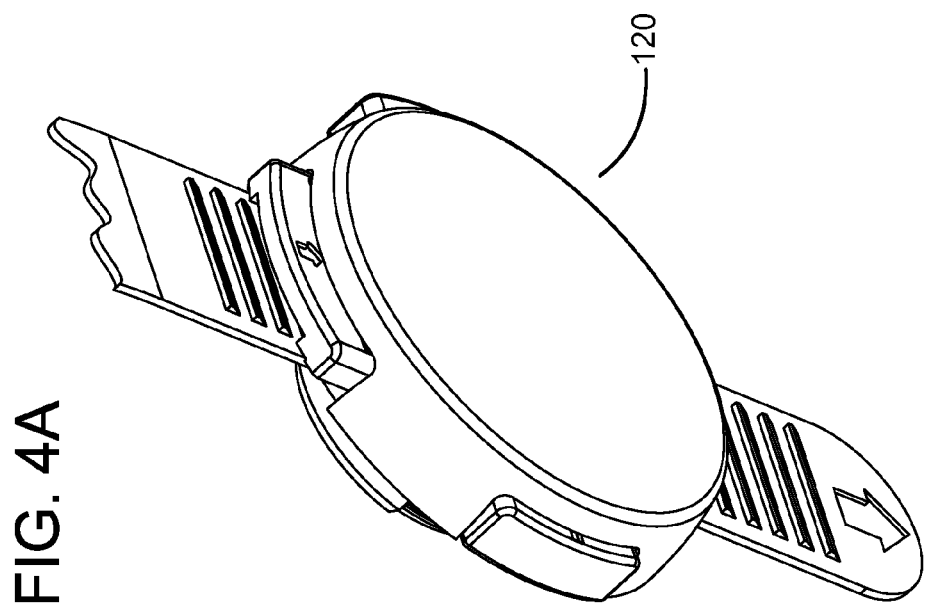
Figure 4C:
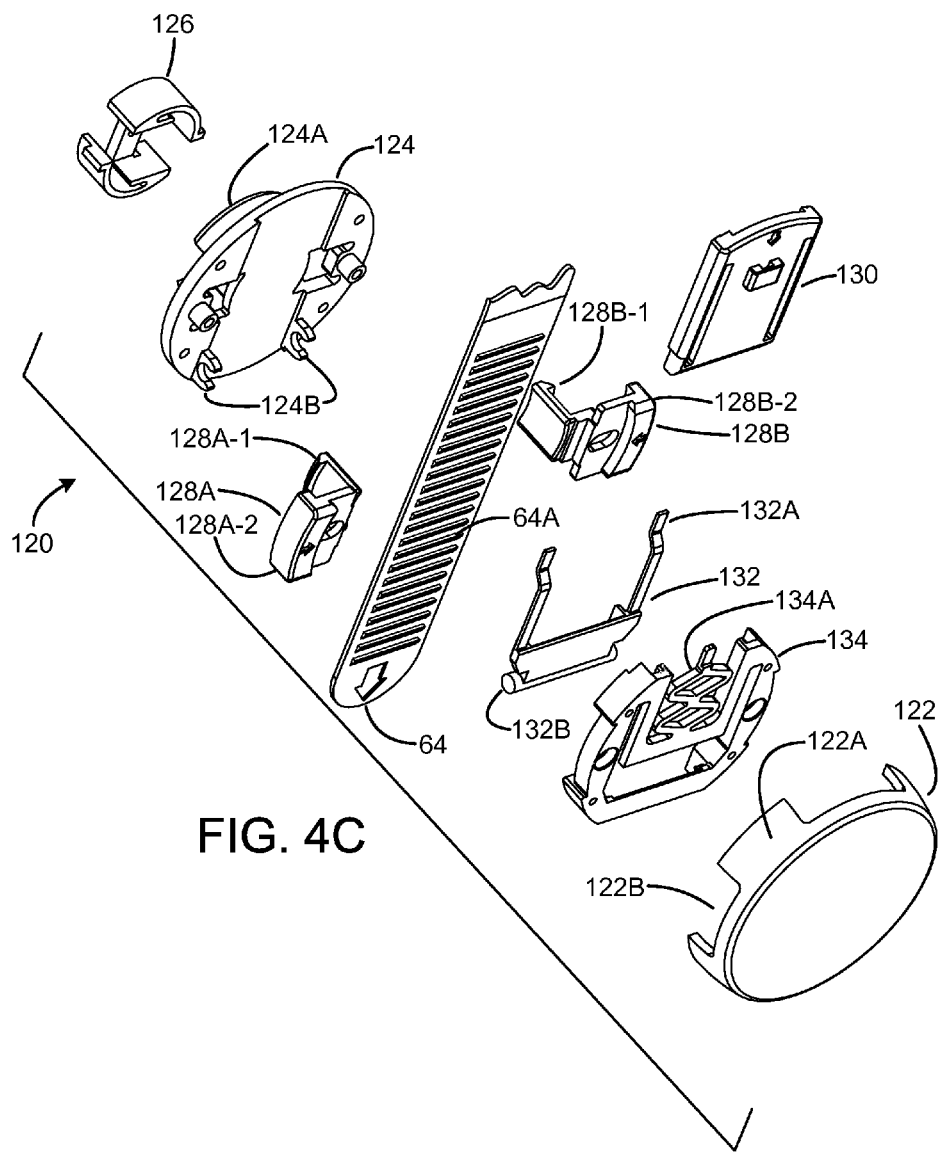
FIG. 4C is an exploded view of the strap connection of FIGS. 4A and 4B.

The adjustment of the effective strap length is provided by engagement of a brake feature 132, carried by connector 120, between back plate 124 and bracket structure 134, between ribs 64A of the strap end 64. As shown in FIG. 4C, for example, the brake feature has opposed pivot portions 132B which are configured to be captured in yoke portions 124B of the back plate 124. Tips or sidearm portions 132A of the brake feature 132 are positioned between the back plate 124 and bracket structure 134. A sliding plate 130 can be pushed inwardly by the user to lift the brake feature 132 out of engagement with the ribs, allowing the strap to be moved within the connector housing to adjust its position. A spring 134A bears against the sliding plate to bias it to the locked position. The brake feature 132 is not affected by pressing the button portions 128A-2, 128B-2 together to release the connector from engagement with the collar body and chin support structure. Thus, the patient or medical staff does not have to adjust the strap each time the collar system is removed from the patient; the existing strap position is maintained.

Figure 5B:
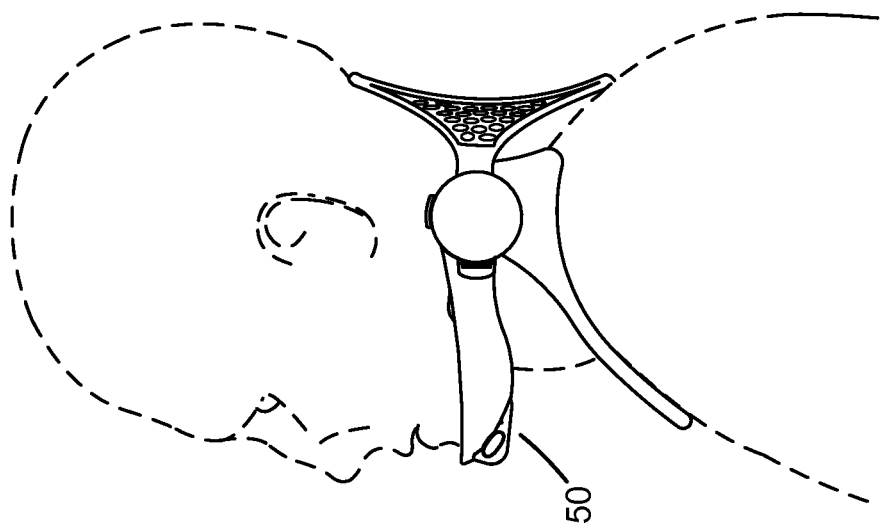
FIGS. 5A and 5B are respective front and left side diagrammatic views illustrating use of a cervical collar as illustrated in FIGS. 1A-4B on a person.
Figure 5A:
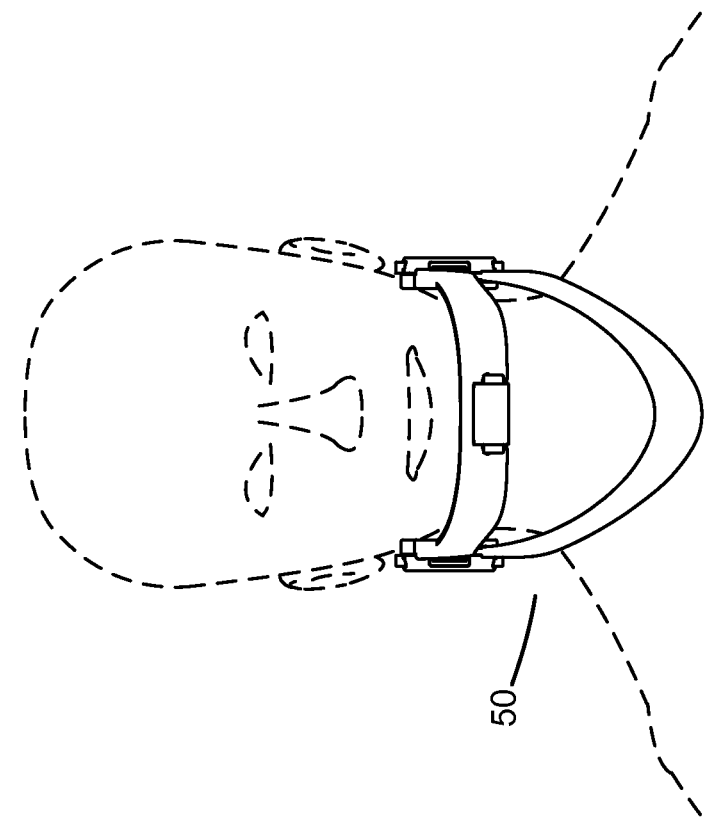

FIGS. 5A and 5B diagrammatically depict an exemplary embodiment of the cervical collar system 50 in position on a person.

Other strap configurations may alternatively be employed, such as straps which connect to the collar body assembly by hook and loop fasteners, or by snaps.

Foam pads may be attached to the chin contacting surface of the chin support structure, and the chest contacting surface of the collar body (e.g. by hook and loop fasteners) to provide additional comfort for the collar wearer. Such pads may be open cell foam pads covered by a fabric layer of a moisture wicking type.

Figure 6A:
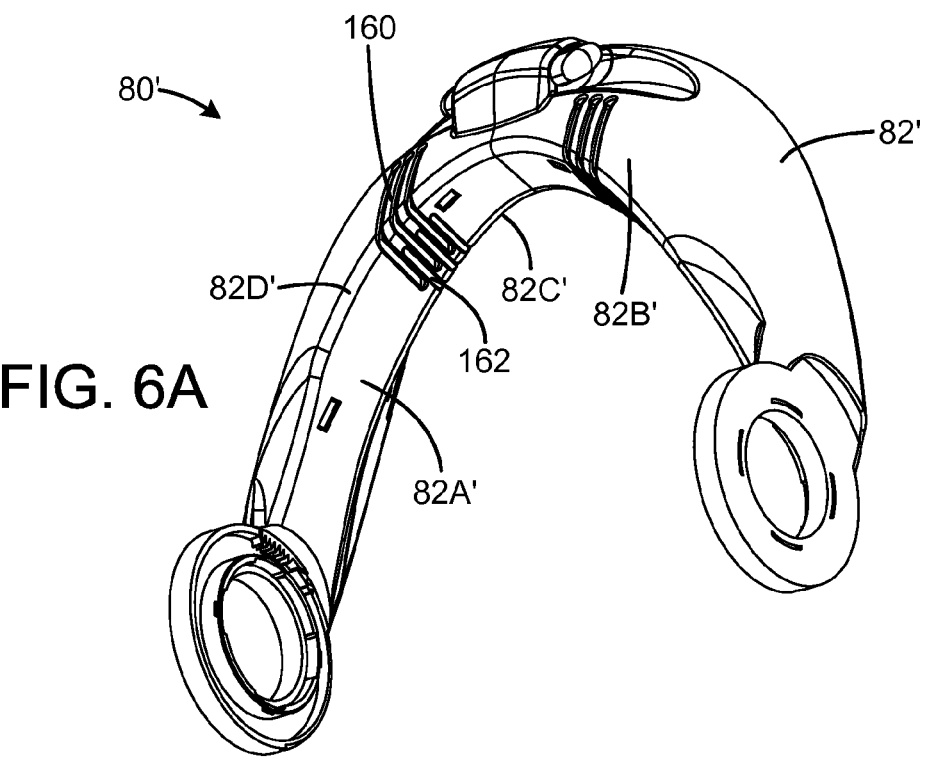
FIGS. 6A and 6B are respective isometric views of an alternate embodiment of a chin support structure, respectively taken from a lower and an upper orientation.
Figure 6B:
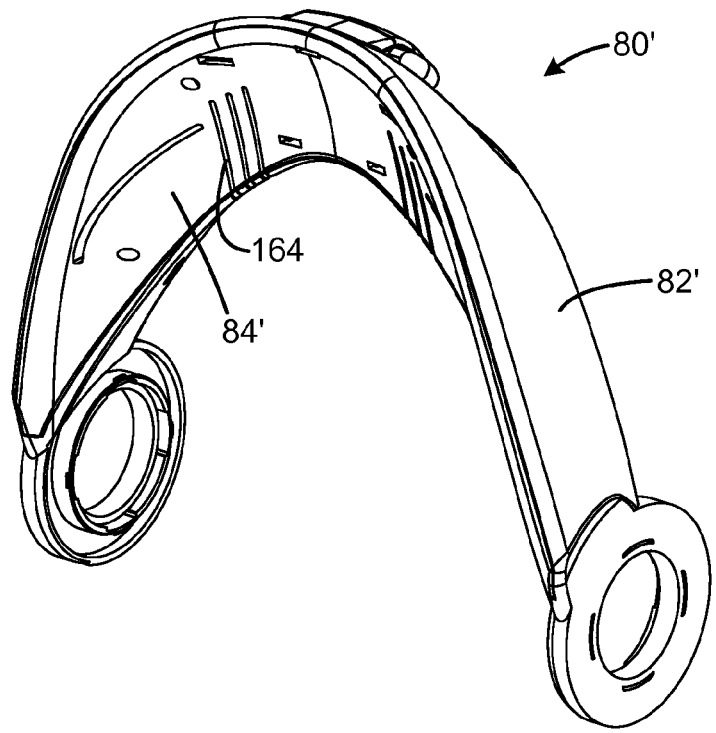

An alternate embodiment of a chin support structure 80' is illustrated in FIGS. 6A and 6B. In this embodiment, the lower housing structure 82' and the upper housing structure 84' are formed with slots to allow the extreme ends of the chin support structure to spread, to accommodate patients with very large necks, and also provide ventilation to a pad attached to the chin supporting surface 84' (e.g. by hook and loop fasteners) and facilitate wicking away moisture. However, the slots are arranged such that the chin support structure 80' remains rigid and provides rigid support to the patient's chin while wearing the collar. Such pads may be open cell foam pads covered by a fabric layer. As with the embodiment of FIGS. 1A-5B, the lower and upper housings structures are unitary, one-piece structures, fabricated by injection molding of a thermoplastic material. The slots are spaced away from the center portion of the chin support structure 80'. The lower housing structure 82' has two sets of slots 160, 162 on each side of the center portion. The slots 162 are formed through a portion of outer curved surface 82B' and extend through a portion of curved interior surface 82A' of the lower housing structure 82', stopping short of the edge 82C'. The slots 162 are formed through interior curved surface 82A' and extend from edge 82C' to an intermediate position between edge 82C' and edge 82D'. Slots 160 and 162 are interleaved. In this embodiment, three each of the slots 160, 162 are formed in the lower housing structure 82' on each side of the center of the chin support structure 82'.

Slots 164 are formed in the upper housing structure 84', as shown in FIG. 6B on opposite sides of the center of the chin support structure, and are respectively aligned with the slots 162 formed in the lower housing structure. The slots 160, 162 and 164 are arranged in a transverse relation to the pivot axis 52 (FIG. 1A) in this exemplary embodiment. In an exemplary embodiment, the slots are about 0.035 inches wide.

In all other respects, the chin support structure 80' is similar to structure 80 of FIGS. 1A-5B, and assembles to the collar body 70 a neck strap in similar fashion.

Pulling apart the extreme ends of the chin support structure 82' when assembled to the collar body 70 allows the extreme ends to be moved apart slightly without cracking or breaking the rigid plastic material of the chin support structure, to allow the collar system to accommodate very wide necks. However, the slots are arranged such that the chin support structure 82' rigidly supports the wearer's chin in vertical and horizontal directions. In an exemplary embodiment, the chin support structure may accommodate up to about two inches of spread.

Figure 7A:
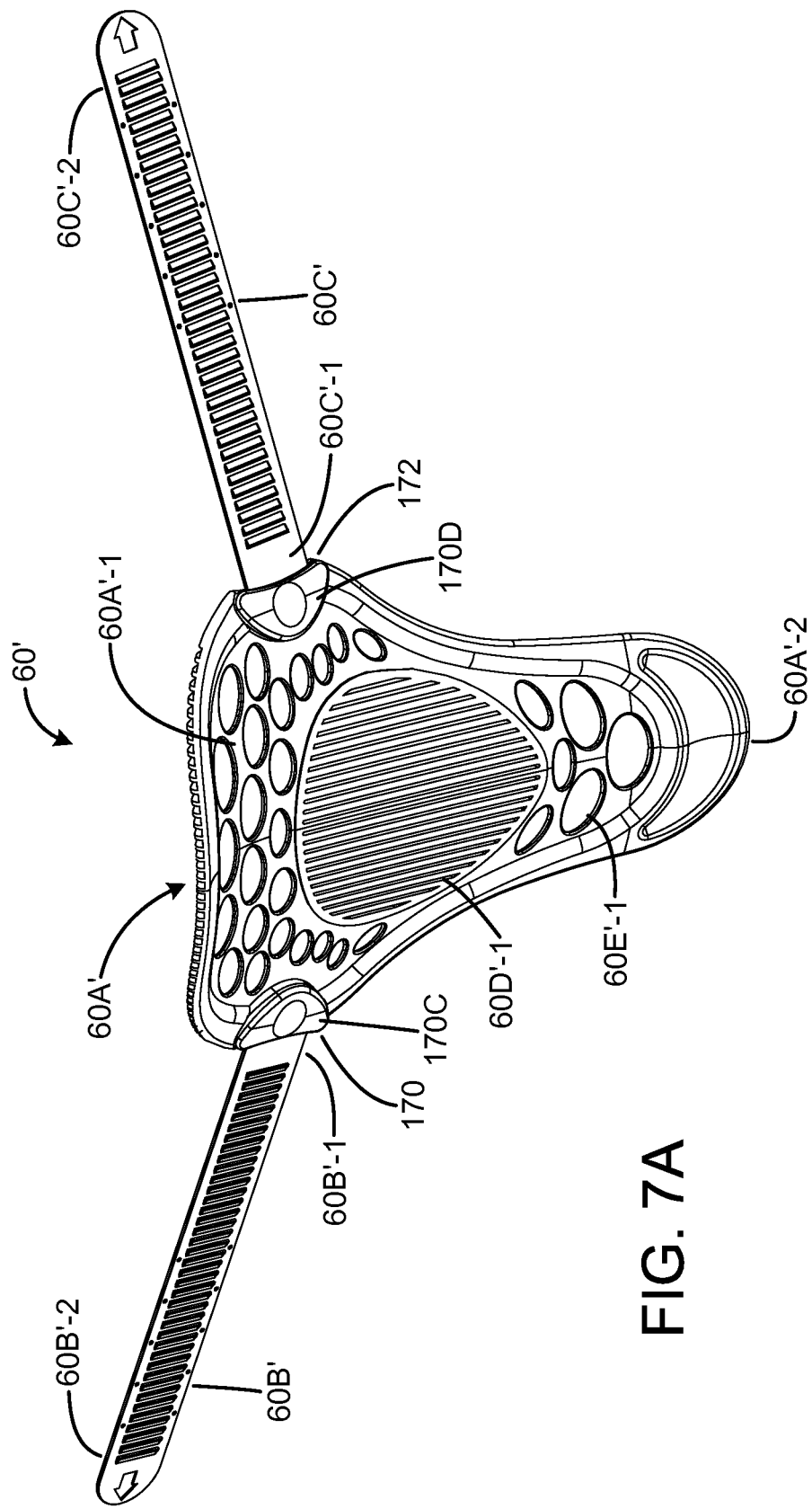
FIGS. 7A and 7B are respective isometric views of an alternate embodiment of a neck strap structure, taken along upper and lower orientations.
Figure 7B:
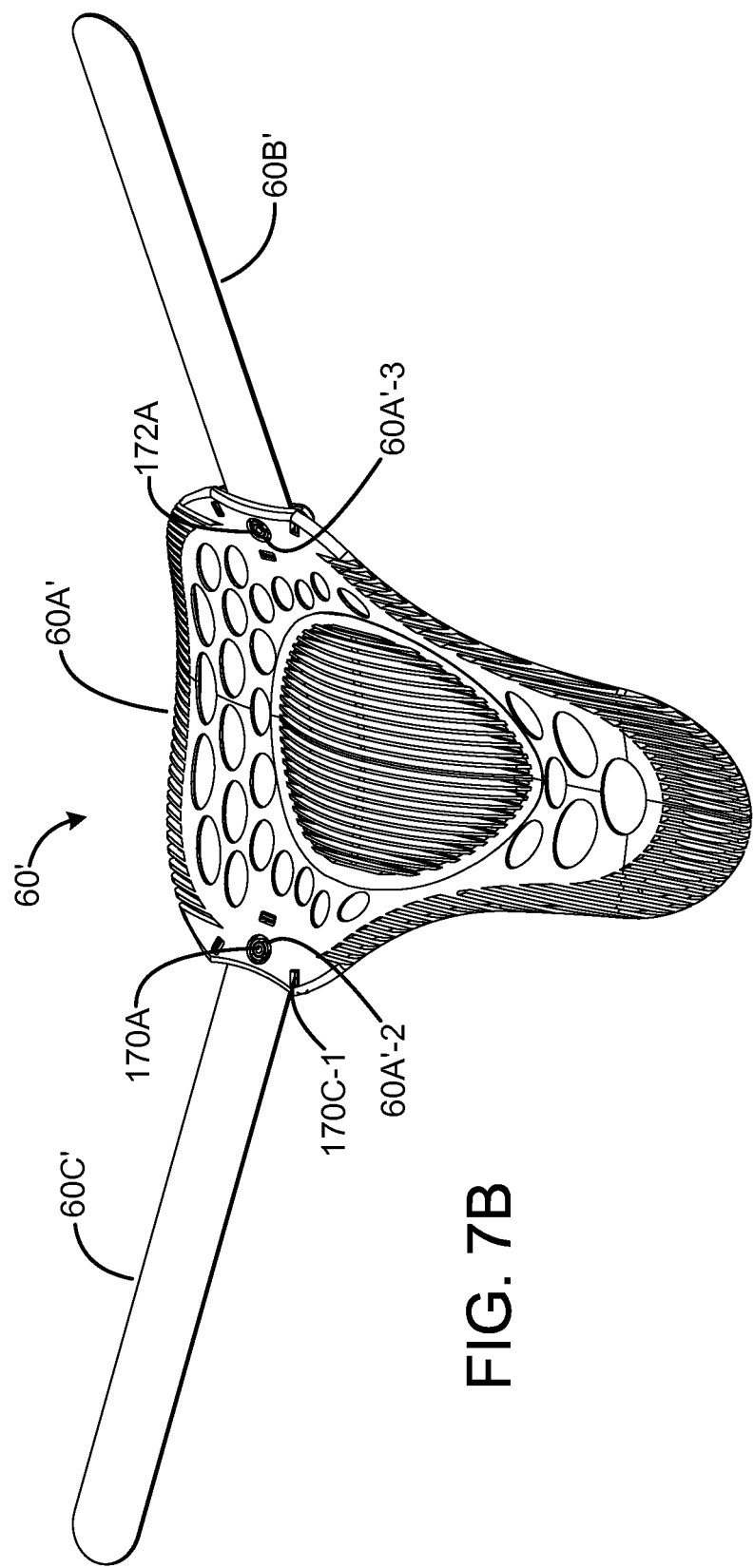
Figure 7C:
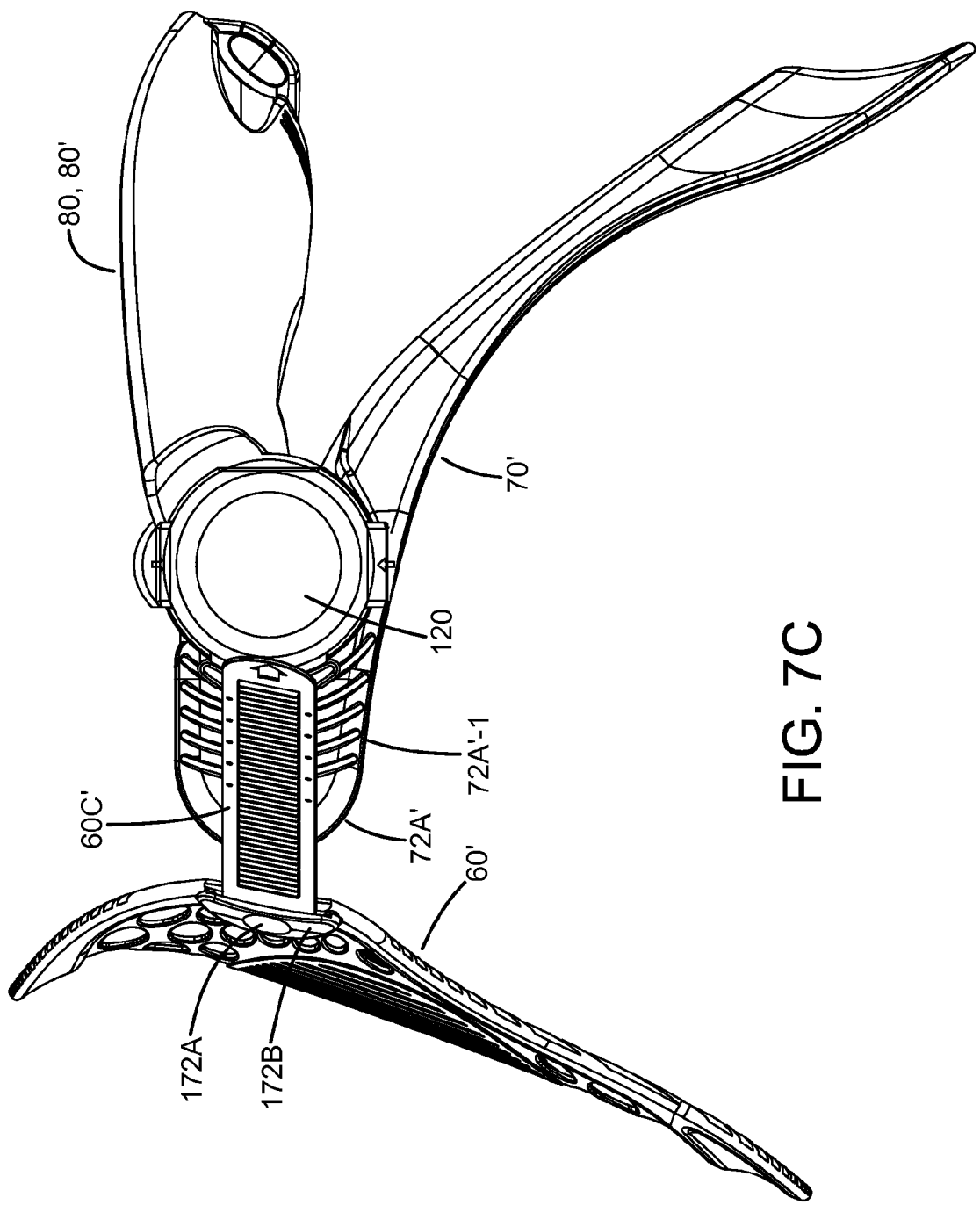
FIG. 7C is a isometric view of a portion of the neck strap structure of FIG. 7A and 7B, in relation to a collar body and chin support structure, with the strap end positioned for insertion into a connector.

An alternate embodiment of a neck strap 60' for the cervical collar 50 is illustrated in FIGS. 7A-7C. Instead of being a single piece structure, the strap 60' is a multi-piece assembly, including a neck pad structure 60A' having a broad top portion 60A'-1 and a narrow lower portion 60A'-2, and two straps 60B' and 60C'. The straps each have a first end which attaches to the broad top portion of the neck pad structure by a pivotal connection 170, 172, and a second end which attaches to a strap connector 120 as with the embodiment of FIGS. 1A-5B.

The pivotal connections 170, 172 may be formed by respective boss structures 170A, 172A integrally formed at the end of the respective strap ends 60B'-1 and 60C'-1, each boss fitted through an opening (60A'-2 or 60A'-3) in the neck pad 60A' Each boss has barbs extending outwardly at distal ends, to capture the boss in place onto the neck pad. Rigid covers 170C and 170D fit over the strap ends 60B'-1 and 60C'-1, and each are secured in place on the neck pad by three spaced, barbed bosses protruding through slots formed in the neck pad. FIG. 7B shows boss 170C-1, for example. The covers provide additional protection against the strap end becoming disconnected from the neck pad, and also provide some frictional engagement against the strap end, tending to hold the strap in a position relative to the neck pad.

The neck pad 60' may be fabricated of a rigid or semi-rigid material, such as nylon or polyethylene. Vertical louvers 60D'-1 are formed in the central region of the neck pad to facilitate flexing or bending of the neck pad to accommodate the contour of the patient's neck region, and the louvers and holes in the neck pad provide ventilation allowing moisture such as perspiration to escape. The covers 170C, 170D are preferably a rigid material such as nylon. The straps are preferably formed of a semi-rigid material having some flexibility, such as nylon.

Figure 7E:
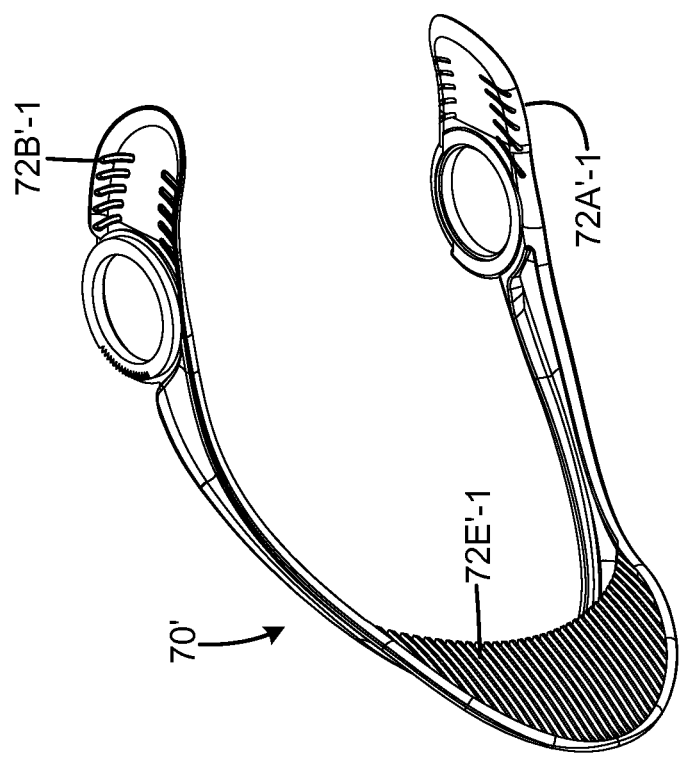
FIGS. 7D and 7E show an alternate embodiment of a collar body structure.
Figure 7D:
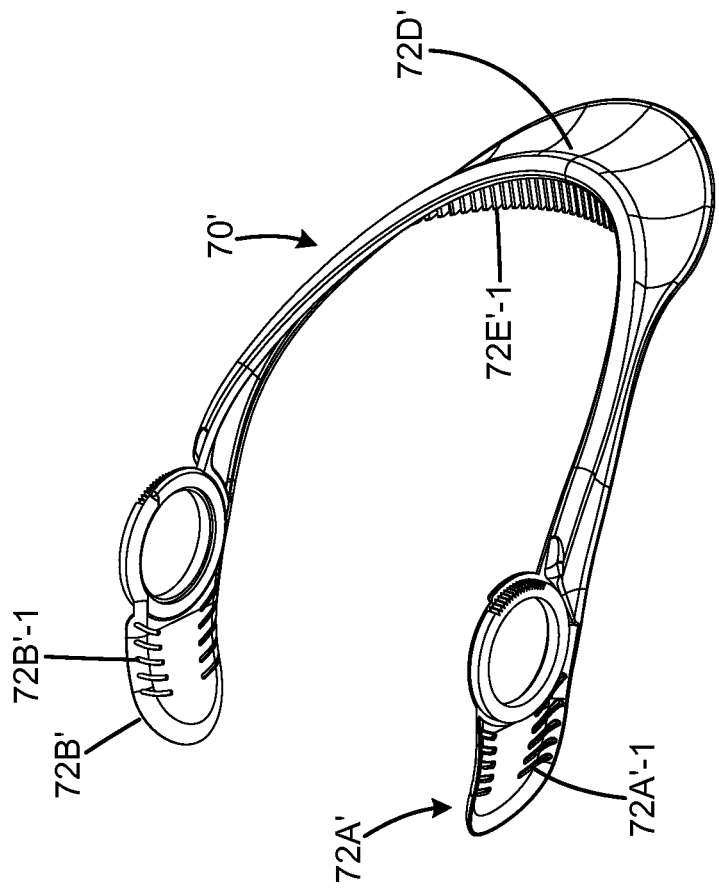

The opposed ends 60B'-2 and 60C'-2 of each strap are inserted into the corresponding strap connector 120 for the system 50, and drawn in to tighten the strap 60' as discussed above regarding the strap 60. FIG. 7C illustrates a portion of the neck pad and strap 60C' in position relative to collar body 70' assembled to chin support structure 80 or 80'. The distal end of the strap is positioned for entry into the connector 120, as described above regarding FIG. 4C. Collar body 70' (shown in FIG. 7D and 7E in further detail) has an extending tab end, such as tab end 72A' extending past the pivot connection with the chin support structure. Slots 72A'-1 are formed in the tab end to facilitate bending of the tab end. The tab ends 72A' and 72B' serve to bridge the gap between the side of the neck pad and the collar body, on patients with larger necks, and to underlay the strap and neck pad on patients with smaller necks, while providing additional circumferential support of the cervical collar structure about the patient's neck.

The pivotal connection of the strap ends to the neck pad structure allows each strap 60B' and 60C' to be pivoted with respect to the neck pad, e.g. by +/−45 degrees or so, and in this embodiment the range of movement is limited by the covers 170C, 170D. The pivotal connection provides another adjustment of the cervical collar on the patient, increasing the patient's comfort.

The alternate embodiment of the collar body 70' is provided with integrally formed spaced fins 72E'-1 to provide some ventilation to a pad attached to the undersurface or fins, e.g. by hook and loop dot fasteners. The fins hold the pad away from the solid surface 72D'-1 of the collar body, allowing moisture such as perspiration to escape from the pad and its moisture-wicking fabric cover.

Figure 7F:
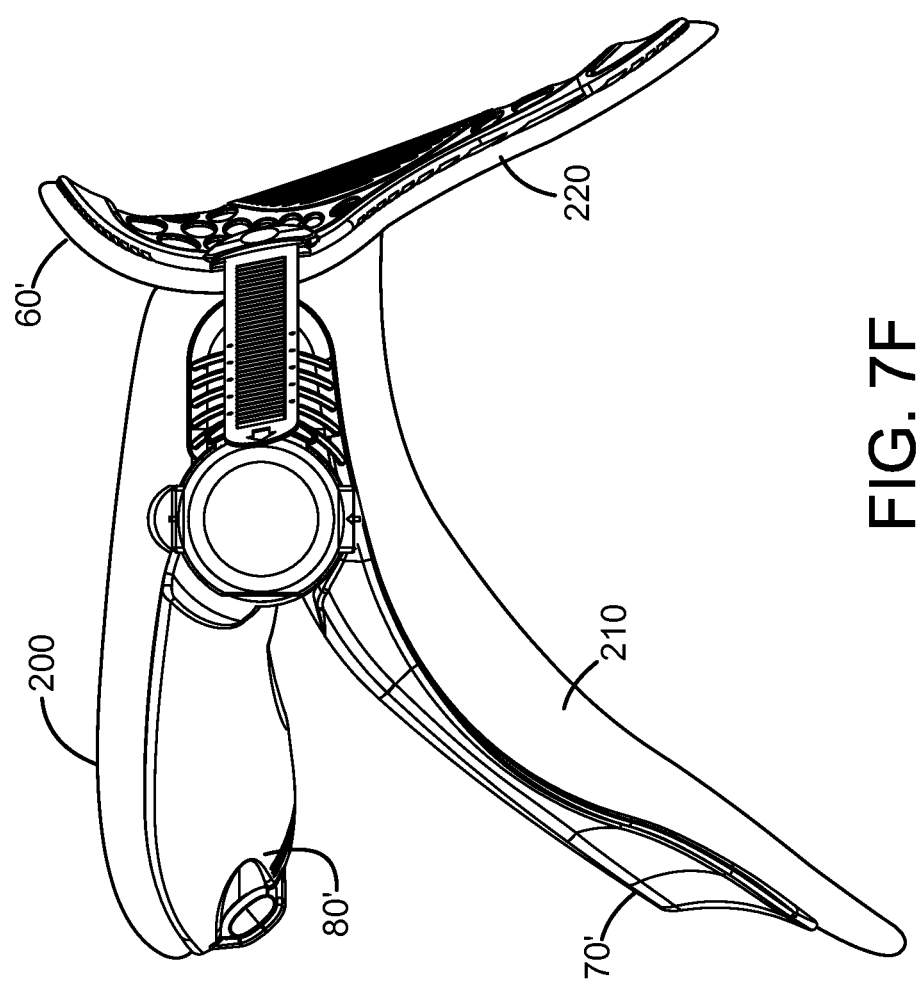
FIG. 7F shows a cervical collar system with foam pads attached.

Pads can be attached to the chin support surface of the chin support structure, to the chest contacting surface of the collar body, and to the neck pad, as illustrated in FIG. 7F. Pad 210 attaches to the underside of the collar body 70', page 200 attaches to the upper surface of the chin support 80', and pad 220 attaches to the inner facing surface of the neck pad 60'. The pads may be attached by hook and loop fasteners, or other attachment mechanisms.

Figure 8:
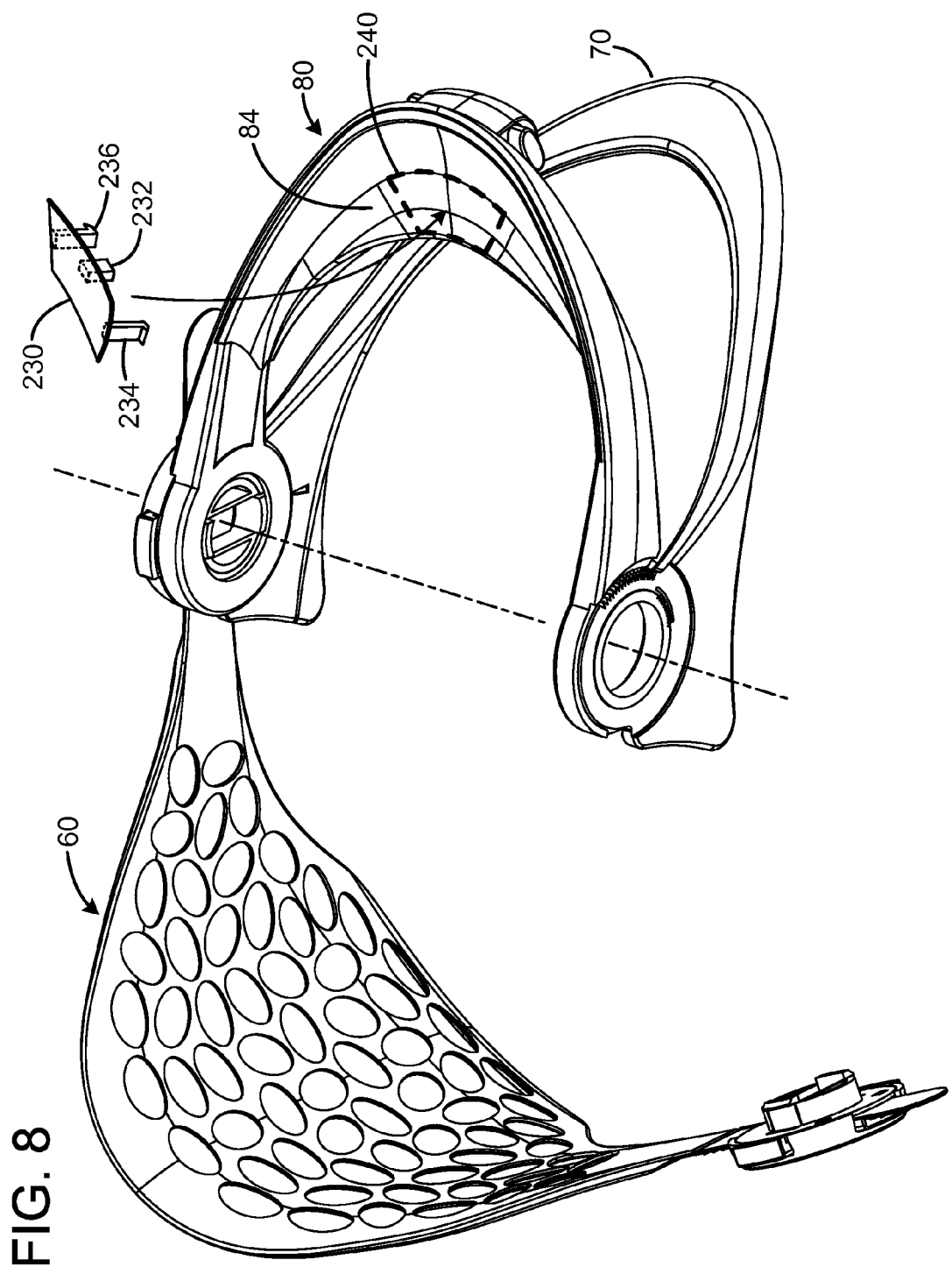
FIGS. 8 illustrates an exemplary embodiment of a lock for preventing operation of a release mechanism for an adjustable collar body system.

Other embodiments of the adjustable collar system may include a means for preventing adjustment of the vertical position of the chin support structure after the position has been set or locked to a desired position. Two exemplary techniques are disclosed for providing a lock for the release mechanism. FIG. 8 illustrates an insert 230 configured for closing an open window 240 formed in the upper structure 84 of the chin support structure 80. The insert 230 has a pin 232 which protrudes into the release mechanism between the arms 114A and 114B, and blocks or prevents the buttons 114A-1 and 114B-1 from being pressed together to rotate the wheel assembly 112. The insert has a pair of locking barbs 234, 236 which will grip the sides of the window 240 to hold the insert in place. Thus, once the medical staff or patient has adjusted the angular position of the chin support 80' relative to the collar body 70 to the proper, desired position, the insert 230 may be inserted in place to close window 240, and block the release buttons from being pressed together to pull the sliding members out of engagement with the teeth on the collar body.

Another technique for preventing further adjustment of the collar body system is illustrated in FIGS. 9A and 9B. Here, a cover 250 is formed of a rigid plastic material, such as polycarbonate, and is formed to fit over the release buttons 114A-1 and 114B-1, preventing access to pinch the buttons together. The cover is molded to the contour of the buttons and boss covering the buttons, and can be a snap fit to assemble to the chin support structure. Barbs or adhesive may be used to further secure the cover 250 in place.

Although the foregoing has been a description and illustration of specific embodiments of the invention, various modifications and changes thereto can be made by persons skilled in the art without departing from the scope and spirit of the invention.

What is claimed is:

1. An adjustable cervical collar system, comprising:
   a collar body; and
   a chin support structure;
   wherein the collar body and chin support structure are assembled together, about respective first and second pivot connections at respective side portions of the collar body and the chin support structure, and arranged for pivotal movement about a pivot axis so that the angle subtended by the collar body and chin support structure can be adjusted through an angular range, and locked in a selected position by a locking mechanism;
   a release mechanism permitting the wearer to easily release the locking mechanism, using one hand in a single action, and allowing the angular position of the chin support structure relative to the collar body to be changed manually by the wearer, and wherein when the release mechanism is released, the locking mechanism automatically locks the chin support in the new position; and
   a neck strap structure comprising a neck pad portion and first and second strap portions;
   a first end of each strap portion arranged to connect to the collar body; and
   wherein second ends of the first and second strap portions are respectively attached to opposed sides of the neck pad portion by a pivot connection allowing the respective first and second strap portions to pivot relative to the neck pad portion through a range of motion to adjust the position of the neck pad relative to the collar body.

2. The system of claim 1,
   wherein the neck strap structure is detachable from the assembly of chin support structure and the collar body, and its effective length is adjustable.

3. The system of claim 2, wherein each first end of the first and second strap portions is removably attached to a respective one of the first and second pivot connections by a respective strap connector.

4. The system of claim 3, wherein each strap connector is configured to allow adjustment of the effective strap length and easy connection and disconnection of the strap connector from the collar body and chin support structure, and also to allow rotation of the strap connector about the pivot connection to the collar body.

5. The system of claim 4, wherein each connector is configured to allow the neck strap to be removed from the collar body and chin support structure without changing the effective strap length, so that the effective strap length is maintained after removal and reattachment of the strap from the collar body and chin support structure.

6. The system of claim 1, wherein the collar body and the chin support structure are rigid structures fabricated from one or more rigid plastic materials.

7. The system of claim 1, further comprising a lock configured to prevent operation of the release mechanism after the angular position has been set to a desired position.

8. An adjustable cervical collar system, comprising:
   a collar body; and
   a chin support structure;
   wherein the collar body and chin support structure are assembled together, about respective first and second pivot connections at respective side portions of the collar body and the chin support structure, and arranged for pivotal movement about a pivot axis so that the angle subtended by the collar body and chin support structure can be adjusted through an angular range, and locked in a selected position by a locking mechanism;
   a release mechanism permitting the wearer to easily release the locking mechanism, using one hand in a single action, and allowing the angular position of the chin support structure relative to the collar body to be changed manually by the wearer, and wherein when the release mechanism is released, the locking mechanism automatically locks the chin support in the new position;
   a neck strap; and
   wherein the neck strap is detachable from the assembly of chin support structure and the collar body, and its effective length is adjustable;
   wherein the neck strap has a first strap end portion and a second strap portion, and each end portion is removably attached to a respective one of the first and second pivot connections by a respective strap connector;
   wherein each strap connector is configured to allow adjustment of the effective strap length and easy connection and disconnection of the strap connector from the collar body and chin support structure, and also to allow rotation of the strap connector about the pivot connection to the collar body; and
   wherein each strap connector comprises:
   a housing;
   a back plate;

respective first and second clip members mounted in the housing and retained by the back plate, each clip member including a button portion and a clip barb feature;

a spring member mounted in a protruding boss feature of the back plate and providing a bias force tending to push the barb features apart;

the barb features of each strap connector configured to pass through an opening in a connector end of the collar body and to clip over an interior surface of the chin support structure, to secure the strap connector in place; and wherein the button portions protrude through slots in the housing structure, and configured so that the user, by pressing the respective button portions together, urge the respective barb portions toward each other and out of engagement with the collar body and chin support structure, allowing the connector to be removed, while also allowing the connector to rotate through a range of motion relative to the collar body.

9. An adjustable cervical collar system, comprising:
a collar body; and
a chin support structure;
wherein the collar body and chin support structure are assembled together, about respective first and second pivot connections at respective side portions of the collar body and the chin support structure, and arranged for pivotal movement about a pivot axis so that the angle subtended by the collar body and chin support structure can be adjusted through an angular range, and locked in a selected position by a locking mechanism;
a release mechanism permitting the wearer to easily release the locking mechanism, using one hand in a single action, and allowing the angular position of the chin support structure relative to the collar body to be changed manually by the wearer, and wherein when the release mechanism is released, the locking mechanism automatically locks the chin support in the new position;
a neck strap; and
wherein the neck strap is detachable from the assembly of chin support structure and the collar body, and its effective length is adjustable;
wherein the neck strap has a first strap end portion and a second strap portion, and each end portion is removably attached to a respective one of the first and second pivot connections by a respective strap connector structure;
wherein each strap connector structure is configured to allow adjustment of the effective strap length and easy connection and disconnection of the strap connector structure from the collar body and chin support structure, and also to allow rotation of the strap connector structure about the pivot connection to the collar body; and
wherein the strap end portions each have a series of ribs, and wherein adjustment of the effective strap length is provided by engagement of a brake feature carried by the connector structure between ribs of the strap end portion, and wherein the connector structure further includes a sliding plate which can be pushed inwardly by the user to allow the brake feature to lift out of engagement with the ribs, allowing the strap end portion to be moved within the connector structure to adjust its position.

10. An adjustable cervical collar system, comprising:
a collar body; and
a chin support structure;
wherein the collar body and chin support structure are assembled together, about respective first and second pivot connections at respective side portions of the collar body and the chin support structure, and arranged for pivotal movement about a pivot axis so that the angle subtended by the collar body and chin support structure can be adjusted through an angular range, and locked in a selected position by a locking mechanism;
a release mechanism permitting the wearer to easily release the locking mechanism, using one hand in a single action, and allowing the angular position of the chin support structure relative to the collar body to be changed manually by the wearer, and wherein when the release mechanism is released, the locking mechanism automatically locks the chin support in the new position; and
wherein the locking mechanism comprises:
an arcuate series of collar body locking teeth formed on each side portion of the collar body, and
a sliding member carried by the chin support member on each side portion and having a set of slider member teeth facing the collar body locking teeth, the sliding member arranged for sliding movement between a locking position in which the slider member teeth are engaged with the collar body locking teeth, and an unlocked position in which the slider member teeth are out of engagement with the collar body locking teeth.

11. The system of claim 10, wherein the locking mechanism comprises a bias spring to apply bias force on each slider member to bias the slider member to the locking position.

12. The system of claim 11, wherein the release mechanism comprises:
respective connector members having respective first ends attached to the respective sliding members;
a mechanism to exert pulling force on the respective connector member to pull the sliding member against the bias force and out of engagement with the collar body locking teeth to release the locking mechanism.

13. The system of claim 12, wherein the mechanism to apply pulling force is carried by the chin support structure, and comprises:
a wheel assembly mounted for rotation about a center shaft, with pins protruding from the wheel assembly at opposed locations adjacent a wheel periphery;
attachment members for connecting ends of the connector members to respective ones of the pins;
actuating arms arranged to engage the wheel assembly at opposed locations and having button portions for contact by a user;
a spring structure arranged to bias the actuating arms apart;
the actuating arms arranged to apply a rotational forced to the wheel assembly when the button portions are pressed toward each other, rotating the wheel assembly and exerting opposed pulling forces on the connector members and thereby on the sliding members, pulling the sliding member teeth out of engagement with the collar body locking teeth and releasing the lock mechanism.

14. An adjustable cervical collar system, comprising:
a collar body; and
a chin support structure;
wherein the collar body and the chin support structure are rigid structures fabricated from one or more rigid plastic materials;
wherein the collar body and chin support structure are assembled together, about respective first and second pivot connections at respective side portions of the collar body and the chin support structure, and arranged for pivotal movement about a pivot axis so that the angle subtended by the collar body and chin support structure can be adjusted through an angular range, and locked in a selected position by a locking mechanism;

a release mechanism permitting the wearer to easily release the locking mechanism, using one hand in a single action, and allowing the angular position of the chin support structure relative to the collar body to be changed manually by the wearer, and wherein when the release mechanism is released, the locking mechanism automatically locks the chin support in the new position; and wherein the chin support structure is formed with a plurality slots to allow the side portions of the chin support structure to spread apart without damaging the chin support structure, the slots also configured to provide ventilation.

15. An adjustable cervical collar system, comprising a rigid collar body structure having opposed side portions;

a rigid chin support structure having opposed side portions and a center portion arranged to support the wearer's chin;

a neck strap structure;

wherein the collar body and chin support structure are assembled together, about respective pivot connections adjacent end of corresponding side portions of the collar body and chin support structure, and arranged for pivotal movement about a pivot axis so that an angle subtended by the collar body and chin support structure is adjustable through an angular range;

a locking mechanism locking the chin support structure in a desired angular position within the angular range relative to the collar body;

a release mechanism actuated by a wearer of the collar system, configured to permit the wearer to easily release the locking mechanism, using one hand, to allow the angular position to be changed manually;

the locking mechanism including a series of collar body teeth carried on each side portion of the collar body and a sliding member carried for sliding movement on each side portion of the chin support structure and having a sliding member teeth, each sliding member arranged for movement between a lock position in which the sliding member teeth engage the collar body teeth and prevent rotation of the chin support structure relative to the collar body, and a release position in which the sliding member teeth are out of engagement with the collar body teeth.

16. The system of claim 15, further comprising a spring member for biasing each sliding member to the lock position, such that when the release mechanism is not actuated, the sliding member is in the lock position.

17. The system of claim 15, wherein the neck strap is detachable from the assembly of the chin support structure and the collar body, and its effective length is adjustable.

18. The system of claim 15, wherein the collar body includes a surface region configured to contact the wearer's chest region, and the collar body includes is integrally formed spaced ventilation fins, configured so that distal edges of the fins space portions of the collar body away from the wearer's chest region.

19. The system of claim 15, wherein the collar body includes a tab end extending past the pivot connection with the chin support structure, to bridge a gap between neck pad and the collar body, on patients with larger necks, and to underlay the strap and neck pad on patients with smaller necks, while providing additional circumferential support of the cervical collar structure about the patient's neck.

20. The system of claim 15, wherein the neck strap structure is a multi-piece assembly, including a neck pad structure and first and second straps each having a first end which attaches to the neck pad structure by a pivotal connection, and a second end which attaches to a strap connector configured for connection to a respective pivot connection between the collar body and the chin support structure, the pivotal connection allowing the respective strap to pivot through a range of motion relative to the neck pad structure.

21. The system of claim 15, wherein the collar body and the chin support structure are rigid structures fabricated from one or more rigid plastic materials.

\* \* \* \* \*